US005834441A

United States Patent [19]
Philip et al.

[11] Patent Number: 5,834,441
[45] Date of Patent: Nov. 10, 1998

[54] ADENO-ASSOCIATED VIRAL (AAV) LIPOSOMES AND METHODS RELATED THERETO

[75] Inventors: Ramila Philip, Redwood City; Jane Lebkowski, Portola Valley, both of Calif.

[73] Assignee: Rhône-Poulenc Rorer Pharmaceuticals Inc., Collegeville, Pa.

[21] Appl. No.: 305,221

[22] Filed: Sep. 12, 1994

Related U.S. Application Data

[63] Continuation-in-part of Ser. No. 120,605, Sep. 13, 1993, abandoned.

[51] Int. Cl.⁶ .......................... A01N 63/00; A61K 48/00; A61K 9/127; C12N 5/00
[52] U.S. Cl. .................... 514/44; 424/93.21; 424/450; 435/69.1; 435/172.3; 435/320.1; 435/325; 536/24.1; 935/22; 935/34; 935/56; 935/60; 935/62; 935/70
[58] Field of Search ...................... 514/44, 2; 435/320.1, 435/235.1, 172.3, 240.2, 69.1, 325; 424/93.1, 93.21, 450; 536/24.1; 935/22, 34, 56, 60, 62, 70

[56] References Cited

U.S. PATENT DOCUMENTS

| | | | |
|---|---|---|---|
| 4,394,488 | 7/1983 | Szoka, Jr. et al. | 435/172 |
| 4,935,372 | 6/1990 | Goh | 435/317.1 |
| 5,126,132 | 6/1992 | Rosenberg | 424/85.2 |
| 5,139,941 | 8/1992 | Muzyczka et al. | 435/172.3 |
| 5,198,344 | 3/1993 | Croop et al. | 435/69.1 |
| 5,250,431 | 10/1993 | Rudd et al. | 435/240.2 |
| 5,252,479 | 10/1993 | Srivastava et al. | 435/235.1 |
| 5,436,146 | 7/1995 | Shenk et al. | 435/172.3 |
| 5,587,308 | 12/1996 | Carter et al. | 435/240.2 |

FOREIGN PATENT DOCUMENTS

| | | |
|---|---|---|
| A 59676/86 | 12/1986 | Australia . |
| 0 206 939 | 12/1986 | European Pat. Off. . |
| 0 405 867 A1 | 1/1991 | European Pat. Off. . |
| A 61 052 286 | 3/1986 | Japan . |
| WO 87/00054 | 1/1987 | WIPO . |
| WO 90/10059 | 9/1990 | WIPO . |
| WO 90/13629 | 11/1990 | WIPO . |
| WO 91/05037 | 4/1991 | WIPO . |
| 9309239 | 5/1993 | WIPO . |
| WO 93/15201 | 8/1993 | WIPO . |
| 9324641 | 12/1993 | WIPO . |

OTHER PUBLICATIONS

JS Cohen (1992) Trends in Biotechnology 10: 87–91.
B Dropulic et al (1994) Human Gene Therapy 5: 927–939.
PA Pizzo et al (1994) Clinical Infectious Diseases 19: 177–196.
ER Kern (1990) In: Antiviral Agents and Viral Diseases of Man, 3rd edition, GJ Galasso et al, eds, pp. 94–95.
Sacramento Bee (Feb. 26, 1994) p. A22.
Sacramento Bee (Nov. 29, 1991) p. B5.
H Collins (Mar. 6, 1993) Philadelphia Inquirer p. A01.
DJ DeNoon (1995) IAC Newsletter DB Accession No. 02944476.
E Tartour et al (1992) Biomedicine and Pharmacotherapy 46: 473–484.
Wang et al., *Proc. Natl. Acad. Sci.*, 84, 7851–7855 (1987).
Marshall, *Science*, 269:1050–1055 (1995).
Hodgson, *Exp. Opin. Ther. Pat.*, 5(5):459–468 (1995).
Miller et al., *F.A.S.E.B.*, 9:190–199 (1995).
Culver et al., *T.I.G.*, 10(5):174–178 (1994).
Rosenberg et al., *Annals Surg.*, 218(4):455–464 (1993).
Gutierrez et al., *Lancet*, 339:715–721 (1992).
Rosenberg, S., *Cancer Res.*, (Suppl.) 51, 5074s–5079s (1991).
Crystal, R., *Science*, 270, 404–410 (1995).
Mulligan, R., *Science*, 260, 926–930 (1993).
Coghlan et al., *New Scientist*, 14–15 (1995).
Brown, D., *The Washington Post*, A22 (Dec. 8, 1995).
Barinaga, M., *Science*, 266, 1326 (1994).
NIH "Report and Recommendations . . . " Dec. 7, 1995, 1–40.
Faller, D.V. and Baltimore, D., *J. Virol.*, 49:269–272 (1984).
Felgner, P.L. et al., *Proc. Natl. Acad. Sci. USA*, 84:7413–7417 (1987).
Rose, J.K. et al., *Biotechniques*, 10:520–525 (1991).
Malone, R. et al., *Proc. Natl. Acad. Sci. USA*, 86:6077–6081 (1989).
Innes, C.L. et al., *J. Virol.*, 64:957–961 (1990).
Philip, R. et al., *J. Biol. Chem.*, 268:16087–16090 (1993).
Shaefer–Ridder, M. et al., *Science*, 215:166–168 (1982).
Stribling, R. et al., *Proc. Natl. Acad. Sci. USA*, 89:11277–11281 (1992).
Zhu, N. et al., *Science*, 261:209–211 (1993).
Stewart, M.J. et al., *Human Gene Therapy*, 3:267–275 (1992).
Felgner et al., *Nature*, 337:387–388 (1989).
Lebkowski, J.S. et al., *Mol. Cell. Biol.*, 8:3988–3996 (1988).
Kotin, R.M. et al., *Proc. Natl. Acad. Sci.*, 87:2211–2215 (1990).
Hermonat, P.L. et al., *J. Virol.*, 51:329–339 (1984).
Graham, F.L. et al., *J. Gen. Virol.*, 36:59–72 (1977).
Hermonat, P.L. and Muzyczka, N., *Proc. Natl. Acad. Sci. USA*, 81:6466–6470 (1984).
Tratschin, J.D. et al., *Mol. Cell. Biol.*, 5:3251–3260 (1985).
Philip, R. et al., *Mol. Cell. Biol.*, 14(4):2411–2418 (1994).
Oken, *Am. J. Clin. Oncol. (CCT)*, 5:649–655 (1982).

(List continued on next page.)

*Primary Examiner*—Bruce R. Campbell
*Attorney, Agent, or Firm*—Synnestvedt & Lechner

[57] ABSTRACT

A composition for genetic manipulation which comprises a liposome comprised of lipid material, and adeno-associated viral (AAV) material. Typically, the AAV material is plasmid, and comprises a terminal repeat of the AAV genome. Methods are disclosed for introducing genetic material into cells by use of AAV liposomes. Accordingly, genetic material was introduced and integrated into stem cells, T cells, primary tumor cells, or tumor cell lines.

49 Claims, 23 Drawing Sheets

OTHER PUBLICATIONS

West, W.H. et al., *N. Engl. J. Med.*, 316:898 (1987).

Topolian, S.L. et al., *J. Immunol. Methods*, 102:127–141 (1987).

Hug et al., *Biochem. Biophys. Acta.*, 1097:1–17 (1991).

Marshall, Science, 269, 1995, 1050–1055.

Hodgson, Exp. Opin. Ther. Pat., 5(5), 1995, 459–468.

Miller et al, FASEB, 9, 1995, 190–199.

Culver et al, TIG, 10(5), 1994, 174–178.

Rosenberg et al, Annals Surg., 218(4), 1993, 455–464.

Gutierrez et, al, The Lancet, 339, 1992, 715–721.

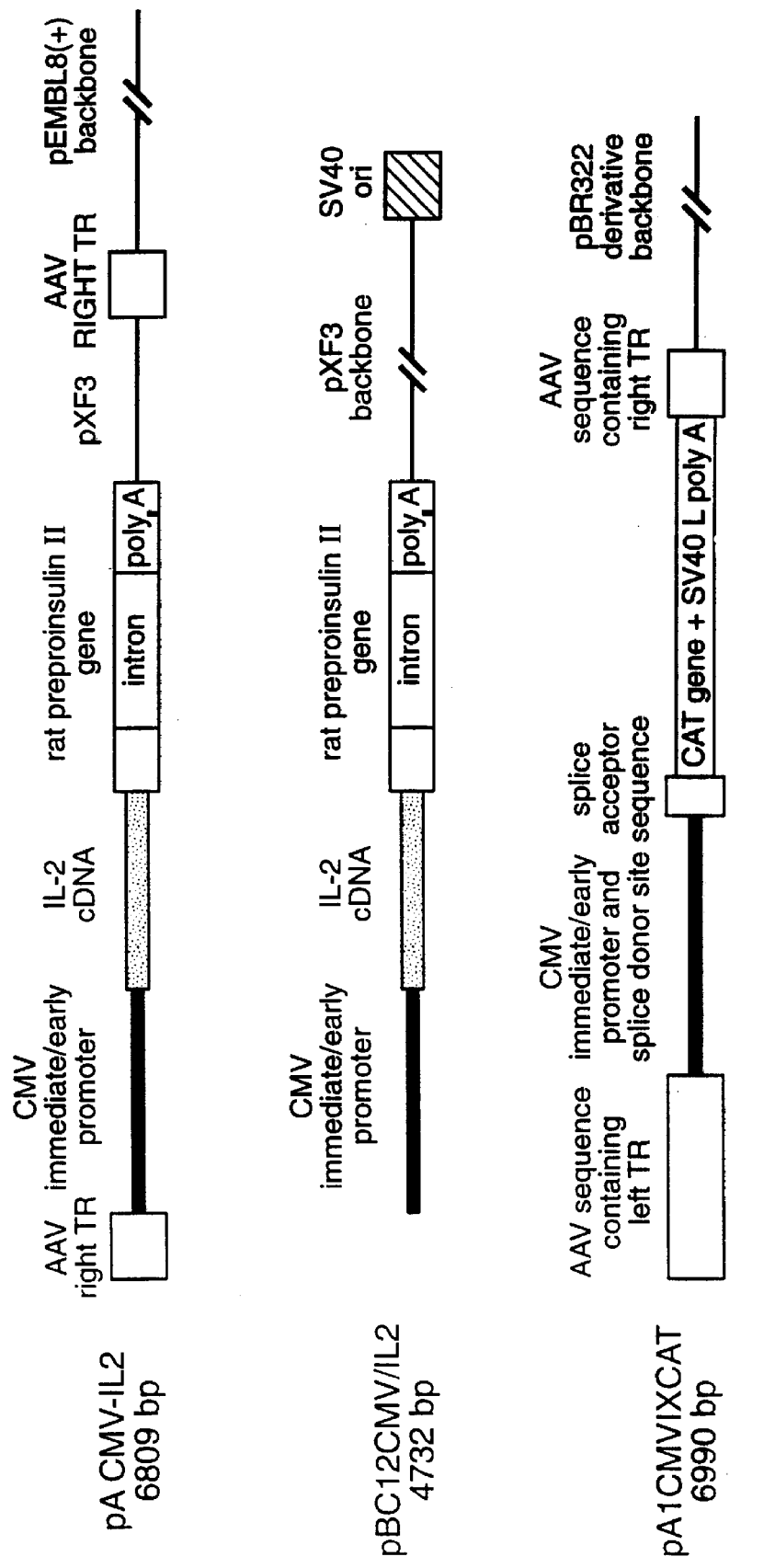
FIG._1

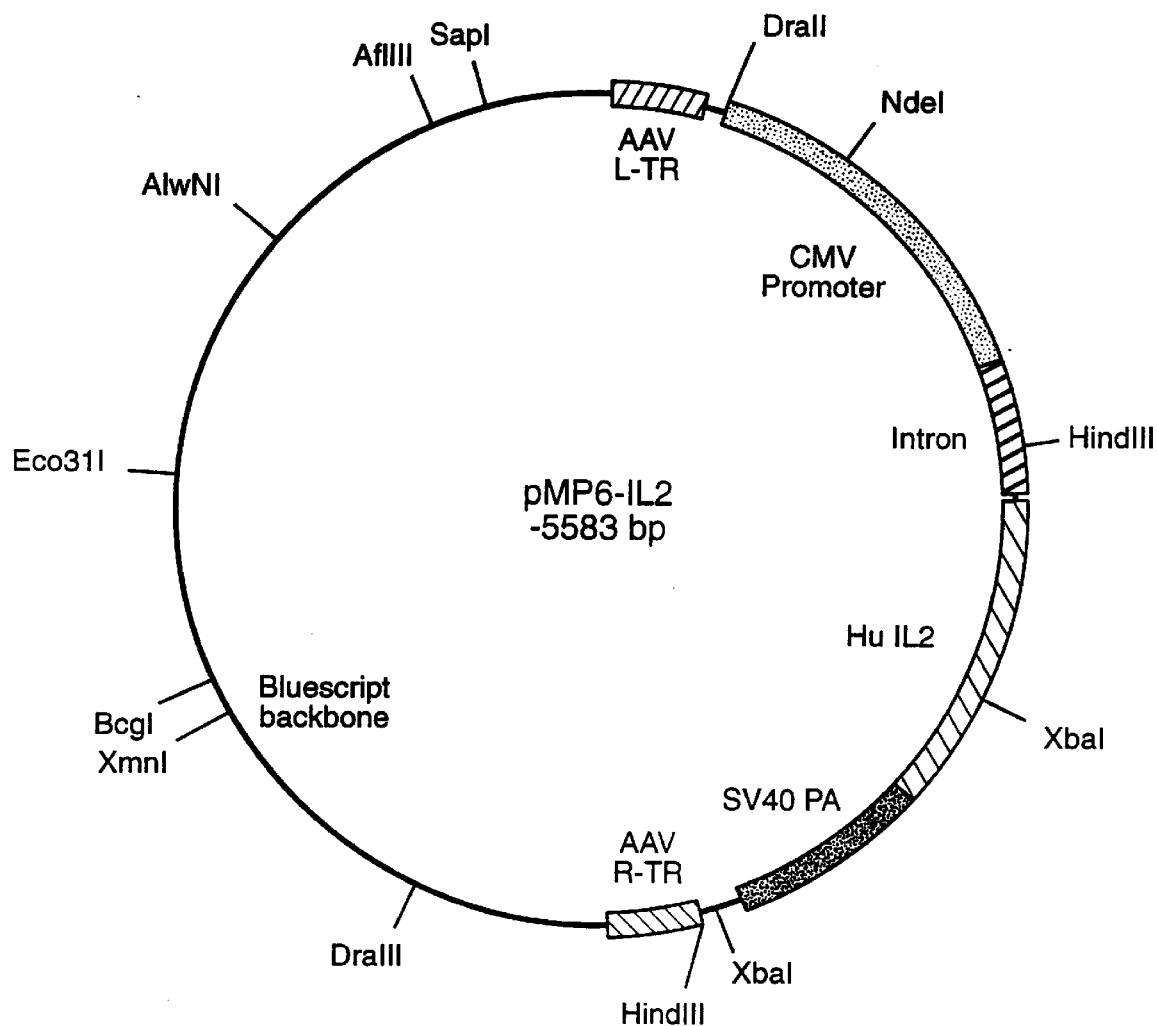
FIG._2

```
  1 CGCGCAATTA ACCCTCACTA AAGGGAACAA AAGCTGGGTA CGATCTGGGC  50
    ◄----------- Bluescript KS II + -----------►----
 51 CACTCCCTCT CTGCGCGCTC GCTCGCTCAC TGAGGACGGG CGACCAAAGG 100
    ----------- Left terminal region of AAV -----------
101 TCGCCCGACG CCCGGGCTTT GCCCGGGCGG CCTCAGTGAG CGAGCGAGCG 150
    --------------------------------------------------
151 CGCAGAGAGG GAGTGGCCAA CTCCATCACT AGGGGTTCCT GGAGGGGTGG 200
    --------------------------------------------------
201 AGTCGTGACG TGAATTACGT CATAGGGTTA GGGAGGTCCG CGCAATTAAC 250
    -----------------------------------------►
251 CCTCACTAAA GGGAACAAAA GCTGGGTACC GGGCCCTTCG ATTCGCCCGA 300
                                                 ►------
301 CATTGATTAT TGACTAGTTA TTAATAGTAA TCAATTACGG GGTCATTAGT 350
    -------------- CMV Promoter --------------
351 TCATAGCCCA TATATGGAGT TCCGCGTTAC ATAACTTACG GTAAATGGCC 400
    --------------------------------------------------
401 CGCCTGGCTG ACCGCCCAAC GACCCCGCC CATTGACGTC AATAATGACG 450
    --------------------------------------------------
451 TATGTTCCCA TAGTAACGCC AATAGGGACT TTCCATTGAC GTCAATGGGT 500
    --------------------------------------------------
501 GGAGTATTTA CGGTAAACTG CCCACTTGGC AGTACATCAA GTGTATCATA 550
    --------------------------------------------------
551 TGCCAAGTAC GCCCCCTATT GACGTCAATG ACGGTAAATG GCCCGCCTGG 600
    --------------------------------------------------
601 CATTATGCCC AGTACATGAC CTTATGGGAC TTTCCTACTT GGCAGTACAT 650
    --------------------------------------------------
651 CTACGTATTA GTCATCGCTA TTACCATGGT GATGCGGTTT TGGCAGTACA 700
    --------------------------------------------------
701 TCAATGGGCG TGGATAGCGG TTTGACTCAC GGGGATTTCC AAGTCTCCAC 750
    --------------------------------------------------
751 CCCATTGACG TCAATGGGAG TTTGTTTTGG CACCAAAATC AACGGGACTT 800
    --------------------------------------------------
801 TCCAAAATGT CGTAACAACT CCGCCCCATT GACGCAAATG GGCGGTAGGC 850
    --------------------------------------------------
851 GTGTACGGTG GGAGGTCTAT ATAAGCAGAG CTCGTTTAGT GAACCGTCAG 900
    --------------------------------------------------
```

FIG._3A

```
901  ATCGCCTGGA GACGCCATCC ACGCTGTTTT GACCTCCATA GAAGACACCG  950

951  GGACCGATCC AGCCTCCGCG GCCGGGAACG GTGCATTGGA ACGCGGATTC  1000

1001 CCCGTGCCAA GAGTGACGTA AGTACCGCCT ATAGAGTCTA TAGGCCCACC  1050

1051 CCCTTGGCTT CTTATGCGAC GGATCAATTC GCTGTCTGCG AGGGCCAGCT  1100
                                ▶|  |◀
1101 GTTGGGGTGA GTACTCCCTC TCAAAAGCGG GCATGACTTC TGCGCTAAGA  1150
     ------- Adeno virus major late intervening sequence --------

1151 TTGTCAGTTT CCAAAAACGA GGAGGATTTG ATATTCACCT GGCCCGCGGT  1200

1201 GATGCCTTTG AGGGTGGCCG CGTCCATCTG GTCAGAAAAG ACAATCTTTT  1250

1251 TGTTGTCAAG CTTGAGGTGT GGCAGGCTTG AGATCTGGCC ATACACTTGA  1300
                    ▶|  |◀

1301 GTGACAATGA CATCCACTTT GCCTTTCTCT CCACAGGTGT CCACTCCCAG  1350
     ------ Mouse immunoglobulin intervening sequence --------

1351 GTCCAACGAT CCACTAGTTC TAGTACCAGC TGCTAGAGCT TGGTAAGTGA  1400
     -----▶|                                            |◀----

1401 CCAGCTACAG TCGGAAACCA TCAGCAAGCA GGTATGTACT CTCCAGGGTG  1450
     --------- Rat preproinsulin 5' untranslated region --------

1451 GGCCTGGCTT CCCCAGTCAA GACTCCAGGG ATTTGAGGGA CGCTGTGGGC  1500

1501 TCTTCTCTTA CATGTACCTT TTGCTAGCCT CAACCCTGAC TATCTTCCAG  1550

1                M  A  L  W  I  D  R  M  Q  L  L  S     12
1551 GTCATTGTTC CAACATGGCC CTGTGGATCG ACAGGATGCA ACTCCTGTCT       1600
     -----------▶|◀-- Rat Insulin --▶|  |◀------------
                    signal peptide
         13  C  I  A  L  S  L  A  L  V  T  N  S  A  P  T  S  S     29
1601 TGCATTGCAC TAAGTCTTGC ACTTGTCACA AACAGTGCAC CTACTTCAAG        1650
     ------------------- Human IL-2 --------------------
         30  S  T  K  K  T  Q  L  Q  L  E  H  L  L  L  D  L       45
1651 TTCTACAAAG AAAACACAGC TACAACTGGA GCATTTACTG CTGGATTTAC       1700

46  Q  M  I  L  N  G  I  N  N  Y  K  N  P  K  L  T  R     62
1701 AGATGATTTT GAATGGAATT AATAATTACA AGAATCCCAA ACTCACCAGG        1750

63  M  L  T  F  K  F  Y  M  P  K  K  A  T  E  L  K  H     79
1751 ATGCTCACAT TTAAGTTTTA CATGCCCAAG AAGGCCACAG AACTGAAACA        1800
```

*FIG._3B*

```
         80    L   Q   C    L   E   E    E   L   K   P    L   E   E    V   L   N     95
       1801   TCTTCAGTGT  CTAGAAGAAG  AACTCAAACC  TCTGGAGGAA  GTGCTAAATT  1850
         96   L   A   Q   S    K   N   F    H   L   R    P   R   D   L    I   S   N    112
       1851   TAGCTCAAAG  CAAAAACTTT  CACTTAAGAC  CCAGGGACTT  AATCAGCAAT  1900
                                     ------- Human IL-2 -------
        113    I   N   V    I   V   L   E    L   K   G    S   E   T    T   F   M   C   129
       1901   ATCAACGTAA  TAGTTCTGGA  ACTAAAGGGA  TCTGAAACAA  CATTCATGTG  1950
        130    E   Y   A    D   E   T    A   T   I   V    E   F   L    N   R   W     145
       1951   TGAATATGCT  GATGAGACAG  CAACCATTGT  AGAATTTCTG  AACAGATGGA  2000
        146    I   T   F   C    Q   S   I    I   S   T    L   T   *
       2001   TTACCTTTTG  TCAAAGCATC  ATCTCAACAC  TGACTTGATA  ATTAAGTGCT  2050

2051   TCCCACTTAA  AACATATCAG  GGATCGATCC  AGACATGATA  AGATACATTG  2100

2101   ATGAGTTTGG  ACAAACCACA  ACTAGAATGC  AGTGAAAAAA  ATGCTTTATT  2150
                          ------- SV40 Polyadenylation signal -------
       2151   TGTGAAATTT  GTGATGCTAT  TGCTTTATTT  GTAACCATTA  TAAGCTGCAA  2200

2201   TAAACAAGTT  AACAACAACA  ATTGCATTCA  TTTTATGTTT  CAGGTTCAGG  2250

2251   GGGAGGTGTG  GGAGGTTTTT  TAAAGCAAGT  AAAACCTCTA  CAAATGTGGT  2300

2301   ATGGCTGATT  ATGATCCGGC  TGCCTCGCGC  GTTTCGGTGA  TGACGGTGAA  2350

2351   AACCTCTGAC  ACATGCAGCT  CCCGGAGACG  GTCACAGCTT  GTCTGTAAGC  2400

2401   GGATGCCGGG  AGCAGACAAG  CCCGTCAGGG  CGCGTCAGCG  GGTGTTGGCG  2450

2451   GGTGTCGGGG  CGCAGCCATG  AGGTCGACTC  TAGTAGAGCG  GCCGCCACCG  2500

2501   CGGTGGAGCT  CCAATTCGCC  CTATAGTGAG  TCGTATTACG  CGCGTCGAGT  2550

2551   CTAGAGAGCT  CGGGCCCAAG  CTTGGTACCC  ATGGCTACGT  AGATAAGTAG  2600

2601   CATGGCGGGT  TAATCATTAA  CTACAAGGAA  CCCCTAGTGA  TGGAGTTGGC  2650
                          ------- Right terminal region of AAV -------
       2651   CACTCCCTCT  CTGCGCGCTC  GCTCGCTCAC  TGAGAGACCG  CGACCAAAGG  2700
```

FIG._3C

```
2701  TCGCCCGACG CCCGGGCTTT GCCCGGGCGG CCTCAGTGAG CGAGCGAGCG  2750

2751  CGCAGAGAGG GACAGATCCA ATTCGCCCTA TAGTGAGTCG TATTACGCGC  2800
              ------►◄----- Bluescript KS II + -----------------

2801  GCTCACTGGC CGTCGTTTTA CAACGTCGTG ACTGGGAAAA CCCTGGCGTT  2850

2851  ACCCAACTTA ATCGCCTTGC AGCACATCCC CCTTTCGCCA GCTGGCGTAA  2900

2901  TAGCGAAGAG GCCCGCACCG ATCGCCCTTC CCAACAGTTG CGCAGCCTGA  2950

2951  ATGGCGAATG GGACGCGCCC TGTAGCGGCG CATTAAGCGC GGCGGGTGTG  3000

3001  GTGGTTACGC GCAGCGTGAC CGCTACACTT GCCAGCGCCC TAGCGCCCGC  3050

3051  TCCTTTCGCT TTCTTCCCTT CCTTTCTCGC CACGTTCGCC GGCTTTCCCC  3100

3101  GTCAAGCTCT AAATCGGGGG CTCCCTTTAG GGTTCCGATT TAGTGCTTTA  3150

3151  CGGCACCTCG ACCCCAAAAA ACTTGATTAG GGTGATGGTT CACGTAGTGG  3200

3201  GCCATCGCCC TGATAGACGG TTTTTCGCCC TTTGACGTTG GAGTCCACGT  3250

3251  TCTTTAATAG TGGACTCTTG TTCCAAACTG GAACAACACT CAACCCTATC  3300

3301  TCGGTCTATT CTTTTGATTT ATAAGGGATT TTGCCGATTT CGGCCTATTG  3350

3351  GTTAAAAAAT GAGCTGATTT AACAAAAATT TAACGCGAAT TTAACAAAA   3400

3401  TATTAACGCT TACAATTTAG GTGGCACTTT TCGGGGAAAT GTGCGCGGAA  3450

3451  CCCCTATTTG TTTATTTTTC TAAATACATT CAAATATGTA TCCGCTCATG  3500

3501  AGACAATAAC CCTGATAAAT GCTTCAATAA TATTGAAAAA GGAAGAGTAT  3550

3551  GAGTATTCAA CATTTCCGTG TCGCCCTTAT TCCCTTTTTT GCGGCATTTT  3600
```

*FIG._3D*

```
3601  GCCTTCCTGT TTTTGCTCAC CCAGAAACGC TGGTGAAAGT AAAAGATGCT  3650

3651  GAAGATCAGT TGGGTGCACG AGTGGGTTAC ATCGAACTGG ATCTCAACAG  3700

3701  CGGTAAGATC CTTGAGAGTT TTCGCCCCGA AGAACGTTTT CCAATGATGA  3750

3751  GCACTTTTAA AGTTCTGCTA TGTGGCGCGG TATTATCCCG TATTGACGCC  3800

3801  GGGCAAGAGC AACTCGGTCG CCGCATACAC TATTCTCAGA ATGACTTGGT  3850

3851  TGAGTACTCA CCAGTCACAG AAAAGCATCT TACGGATGGC ATGACAGTAA  3900

3901  GAGAATTATG CAGTGCTGCC ATAACCATGA GTGATAACAC TGCGGCCAAC  3950

3951  TTACTTCTGA CAACGATCGG AGGACCGAAG GAGCTAACCG CTTTTTTGCA  4000

4001  CAACATGGGG GATCATGTAA CTCGCCTTGA TCGTTGGGAA CCGGAGCTGA  4050

4051  ATGAAGCCAT ACCAAACGAC GAGCGTGACA CCACGATGCC TGTAGCAATG  4100

4101  GCAACAACGT TGCGCAAACT ATTAACTGGC GAACTACTTA CTCTAGCTTC  4150

4151  CCGGCAACAA TTAATAGACT GGATGGAGGC GGATAAAGTT GCAGGACCAC  4200

4201  TTCTGCGCTC GGCCCTTCCG GCTGGCTGGT TTATTGCTGA TAAATCTGGA  4250

4251  GCCGGTGAGC GTGGGTCTCG CGGTATCATT GCAGCACTGG GGCCAGATGG  4300

4301  TAAGCCCTCC CGTATCGTAG TTATCTACAC GACGGGGAGT CAGGCAACTA  4350

4351  TGGATGAACG AAATAGACAG ATCGCTGAGA TAGGTGCCTC ACTGATTAAG  4400

4401  CATTGGTAAC TGTCAGACCA AGTTTACTCA TATATACTTT AGATTGATTT  4450

4451  AAAACTTCAT TTTTAATTTA AAAGGATCTA GGTGAAGATC CTTTTTGATA  4500
```

FIG._3E

```
4501  ATCTCATGAC CAAAATCCCT TAACGTGAGT TTTCGTTCCA CTGAGCGTCA  4550
4551  GACCCCGTAG AAAAGATCAA AGGATCTTCT TGAGATCCTT TTTTTCTGCG  4600
4601  CGTAATCTGC TGCTTGCAAA CAAAAAAACC ACCGCTACCA GCGGTGGTTT  4650
4651  GTTTGCCGGA TCAAGAGCTA CCAACTCTTT TTCCGAAGGT AACTGGCTTC  4700
4701  AGCAGAGCGC AGATACCAAA TACTGTCCTT CTAGTGTAGC CGTAGTTAGG  4750
4751  CCACCACTTC AAGAACTCTG TAGCACCGCC TACATACCTC GCTCTGCTAA  4800
4801  TCCTGTTACC AGTGGCTGCT GCCAGTGGCG ATAAGTCGTG TCTTACCGGG  4850
4851  TTGGACTCAA GACGATAGTT ACCGGATAAG GCGCAGCGGT CGGGCTGAAC  4900
4901  GGGGGGTTCG TGCACACAGC CCAGCTTGGA GCGAACGACC TACACCGAAC  4950
4951  TGAGATACCT ACAGCGTGAG CTATGAGAAA GCGCCACGCT TCCCGAAGGG  5000
5001  AGAAAGGCGG ACAGGTATCC GGTAAGCGGC AGGGTCGGAA CAGGAGAGCG  5050
5051  CACGAGGGAG CTTCCAGGGG GAAACGCCTG GTATCTTTAT AGTCCTGTCG  5100
5101  GGTTTCGCCA CCTCTGACTT GAGCGTCGAT TTTTGTGATG CTCGTCAGGG  5150
5151  GGGCGGAGCC TATGGAAAAA CGCCAGCAAC GCGGCCTTTT TACGGTTCCT  5200
5201  GGCCTTTTGC TGGCCTTTTG CTCACATGTT CTTTCCTGCG TTATCCCCTG  5250
5251  ATTCTGTGGA TAACCGTATT ACCGCCTTTG AGTGAGCTGA TACCGCTCGC  5300
5301  CGCAGCCGAA CGACCGAGCG CAGCGAGTCA GTGAGCGAGG AAGCGGAAGA  5350
5351  GCGCCCAATA CGCAAACCGC CTCTCCCCGC GCGTTGGCCG ATTCATTAAT  5400
```

*FIG._3F*

5401 GCAGCTGGCA CGACAGGTTT CCCGACTGGA AAGCGGGCAG TGAGCGCAAC 5450
5451 GCAATTAATG TGAGTTAGCT CACTCATTAG GCACCCCAGG CTTTACACTT 5500
5501 TATGCTTCCG GCTCGTATGT TGTGTGGAAT TGTGAGCGGA TAACAATTTC 5550
           ----------- Bluescript KS II + -----------------
5551 ACACAGGAAA CAGCTATGAC CATGATTACG CCAAG 5585
FIG._3G
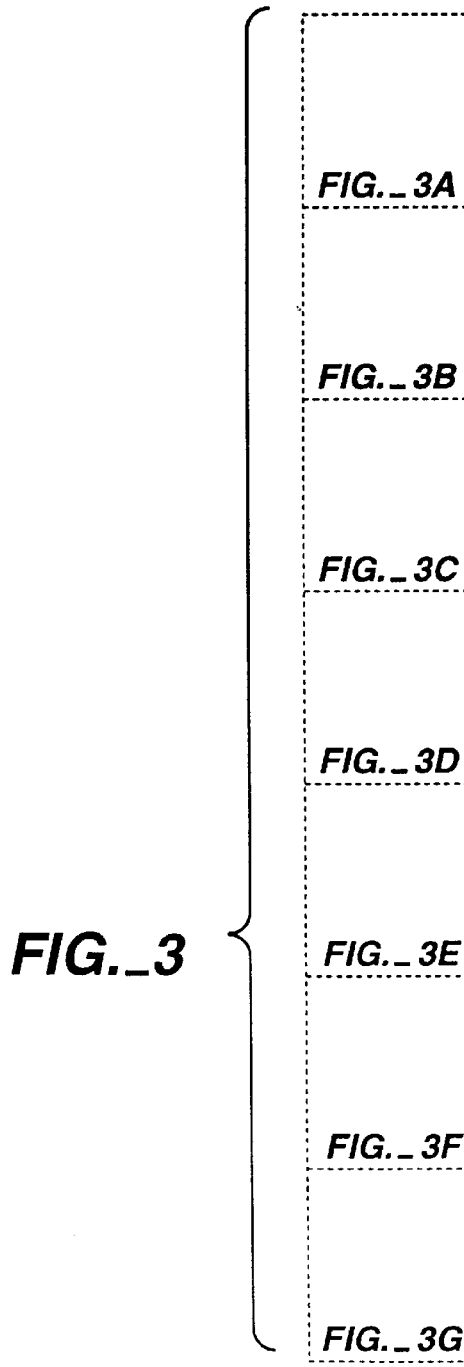
FIG._3
FIG._3A
FIG._3B
FIG._3C
FIG._3D
FIG._3E
FIG._3F
FIG._3G

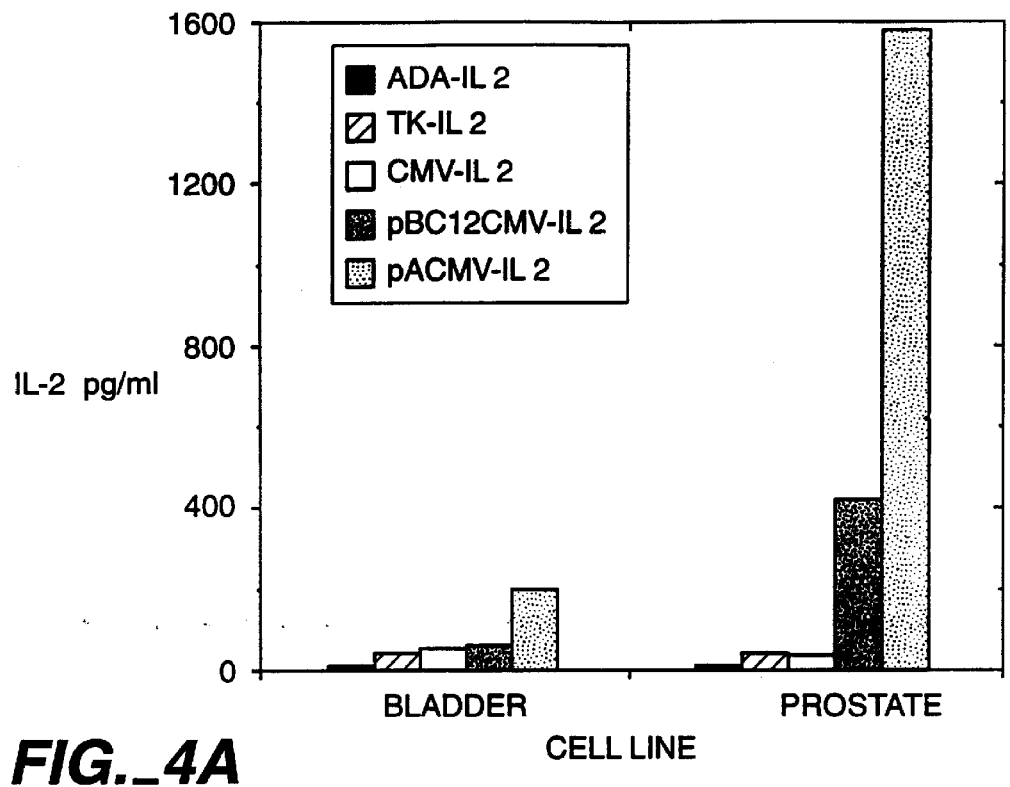
FIG._4A
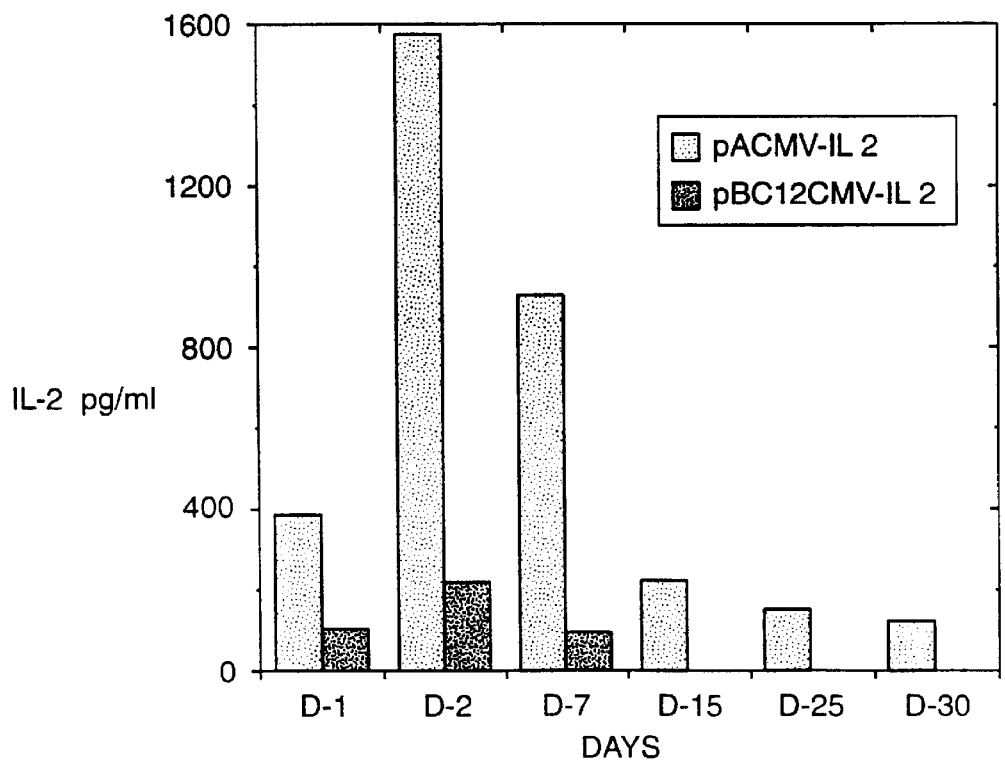
FIG._4B

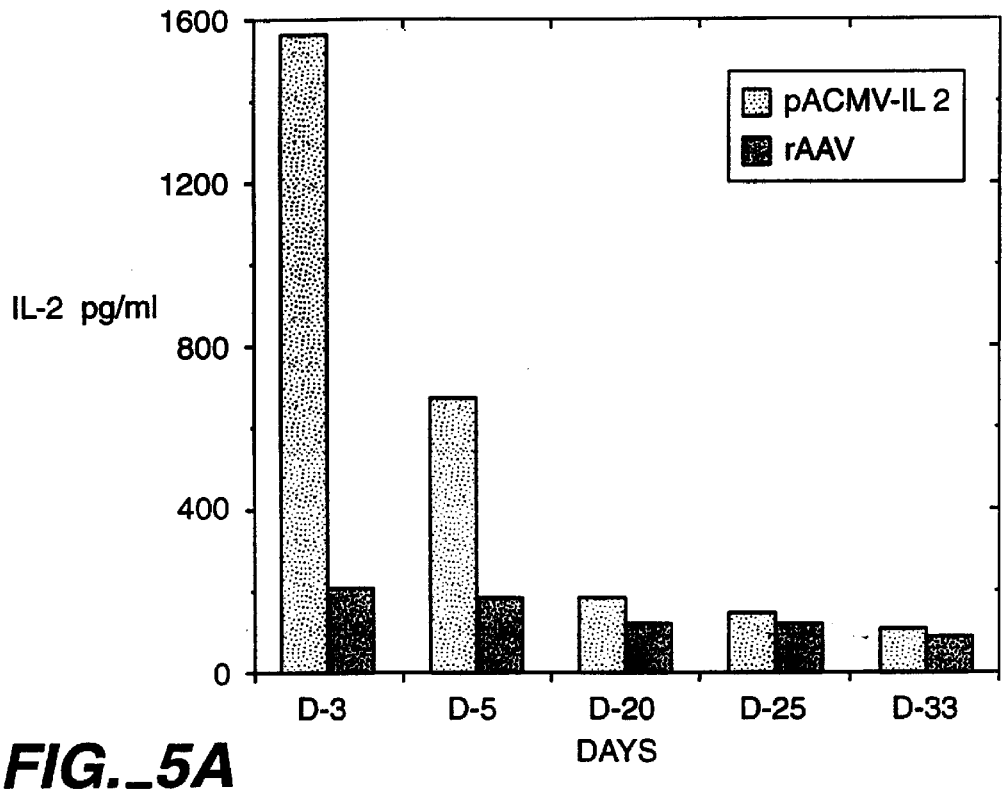
FIG._5A
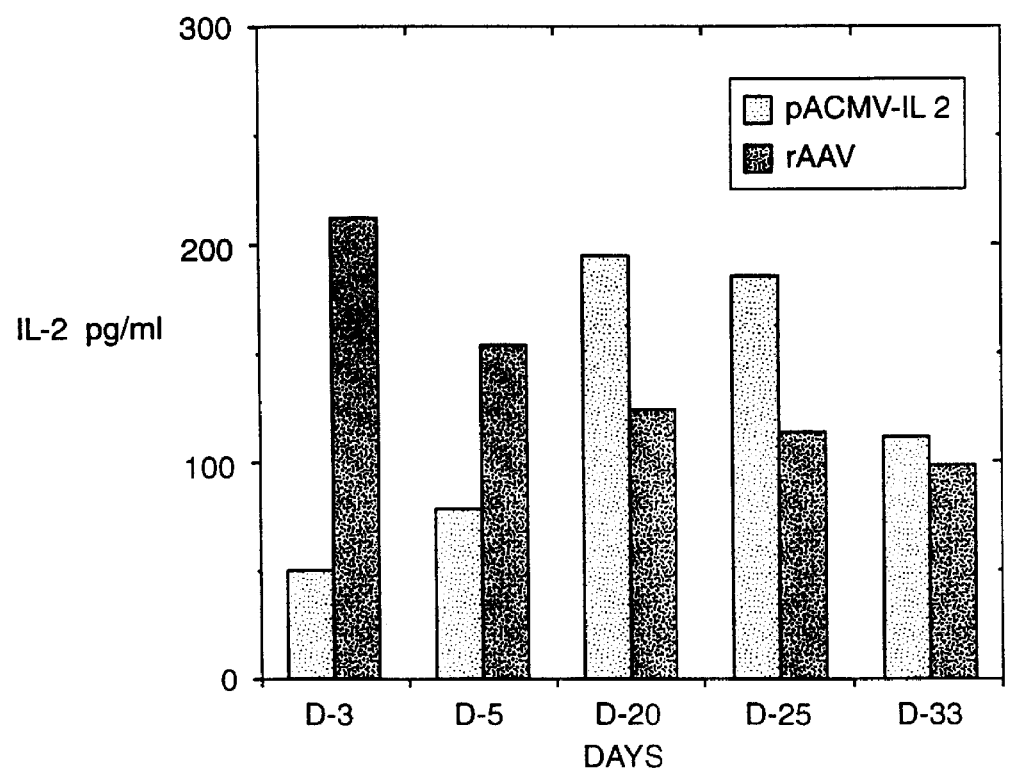
FIG._5B

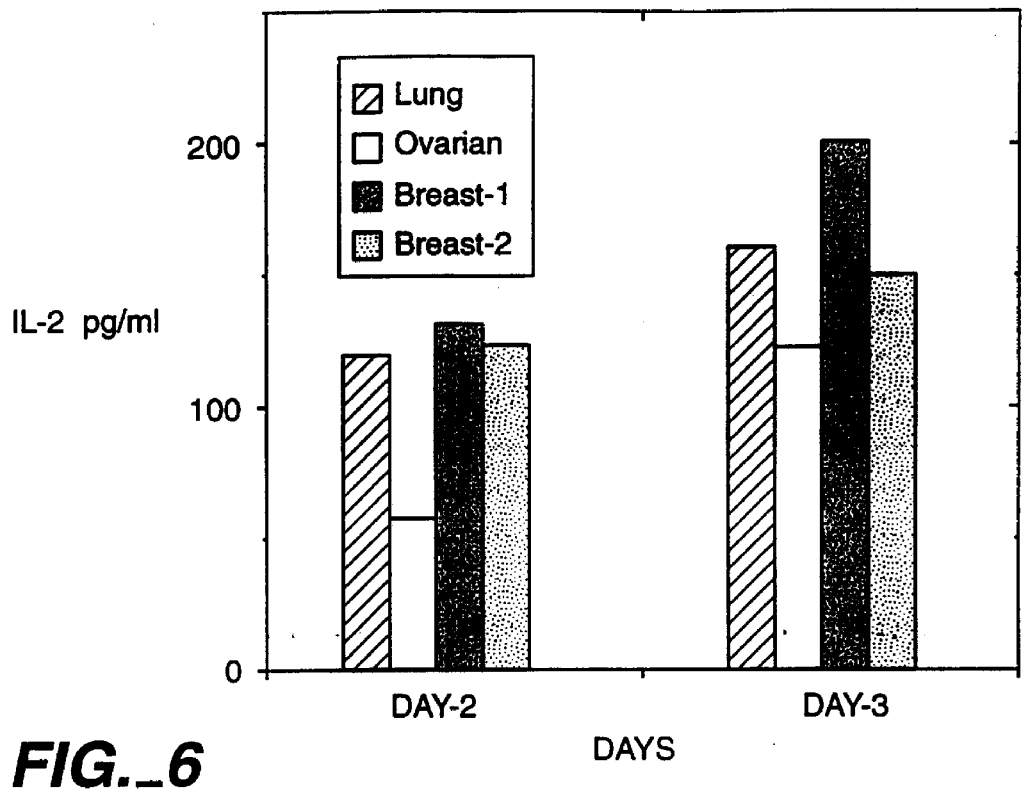
FIG._6
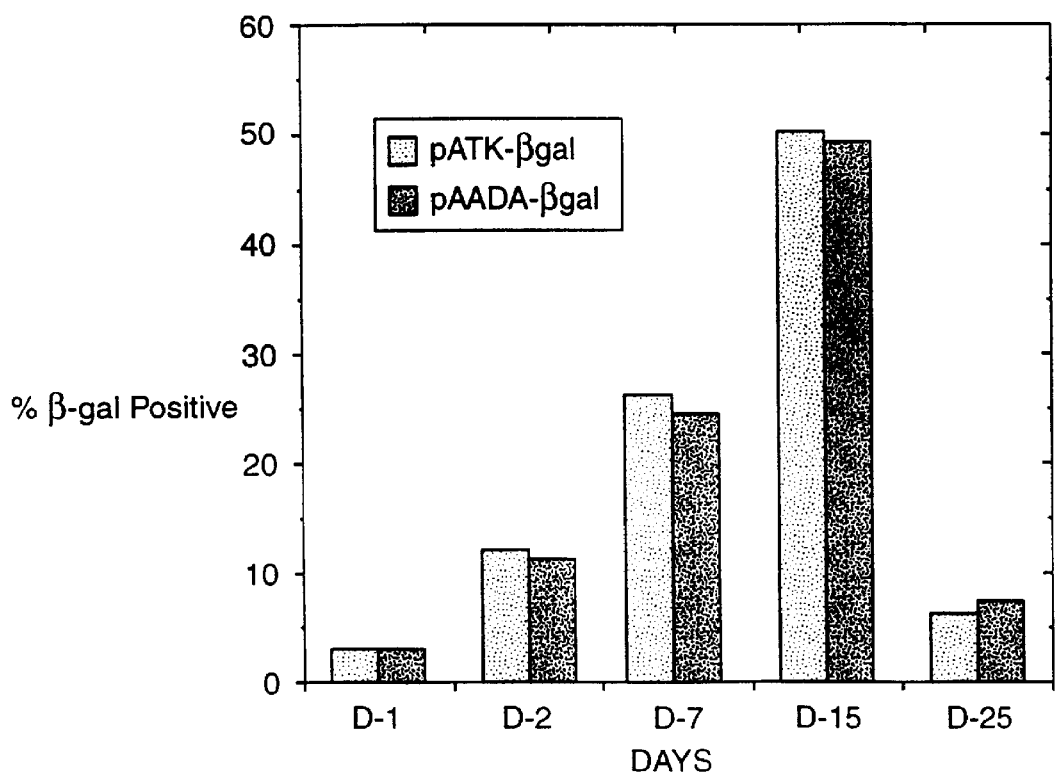
FIG._8

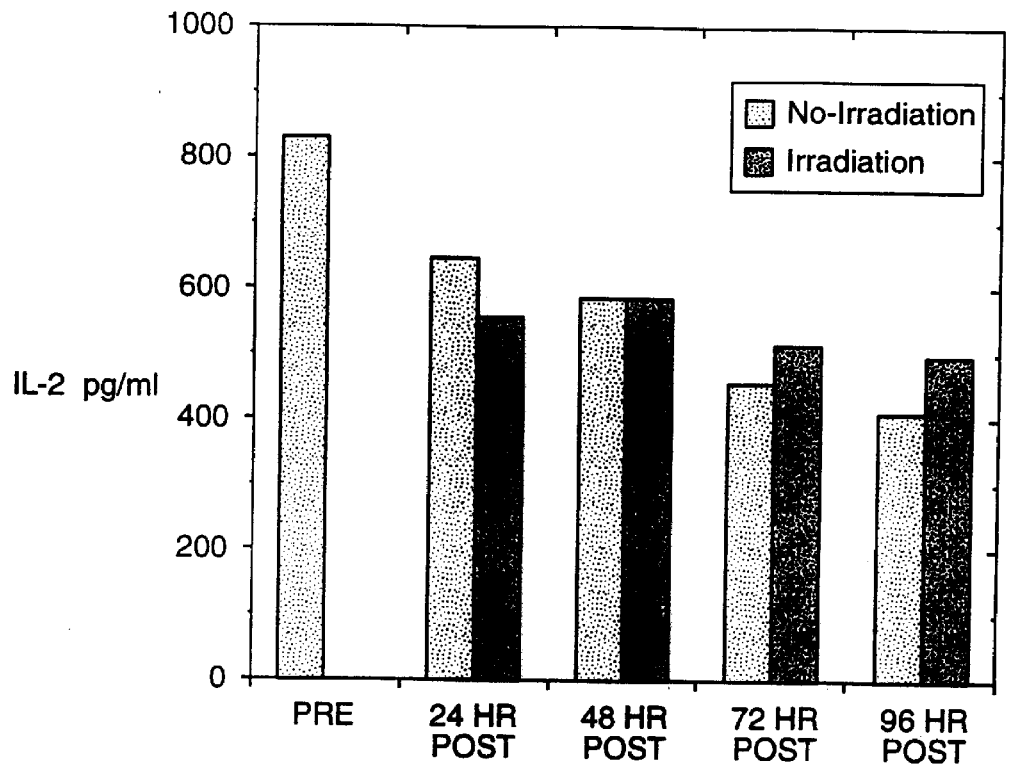
FIG._7A
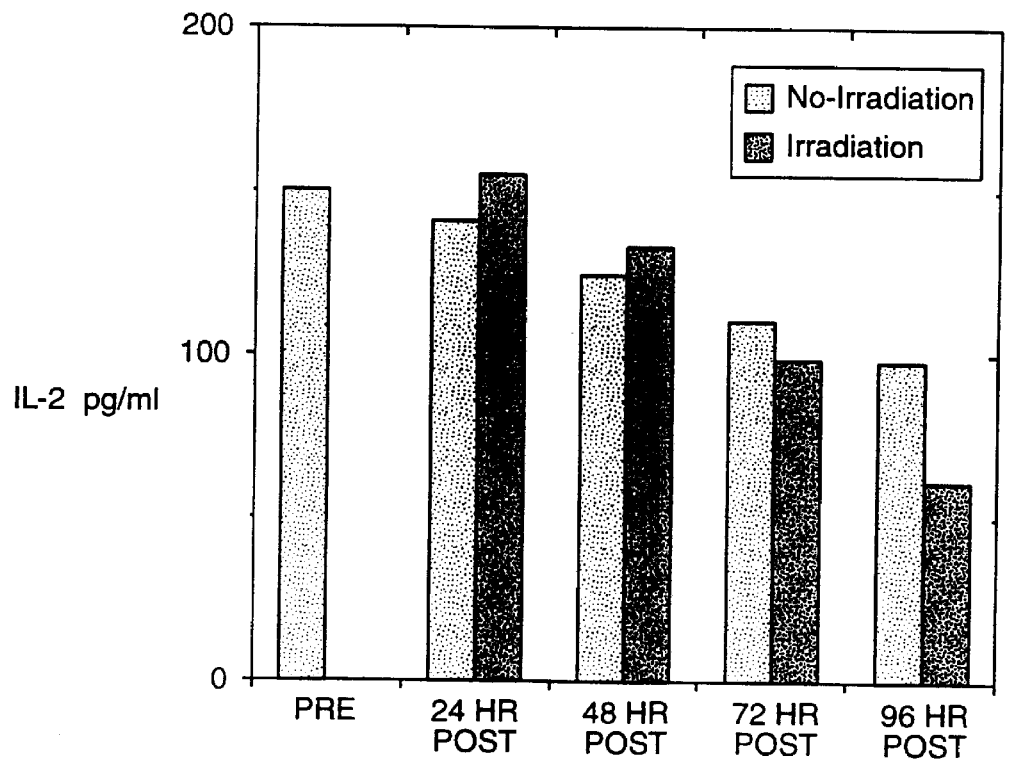
FIG._7B

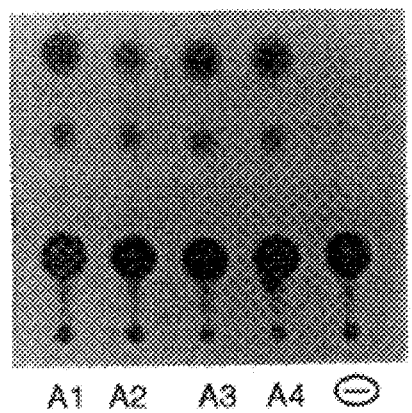
d2
FIG._9A
① 10 μg PACMVIXCAT + 10 nmole D as D:D 1:1
② 10 μg PACMVIXCAT + 20 nmole D as D:D 1:1
③ 10 μg PACMVIXCAT + 10 nmole D as D:C 1:1
④ 10 μg PACMVIXCAT + 20 nmole D as D:C 1:1
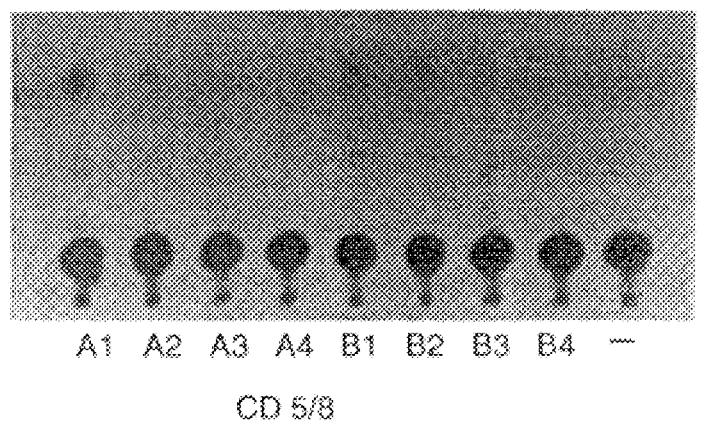
CD 5/8
FIG._9B

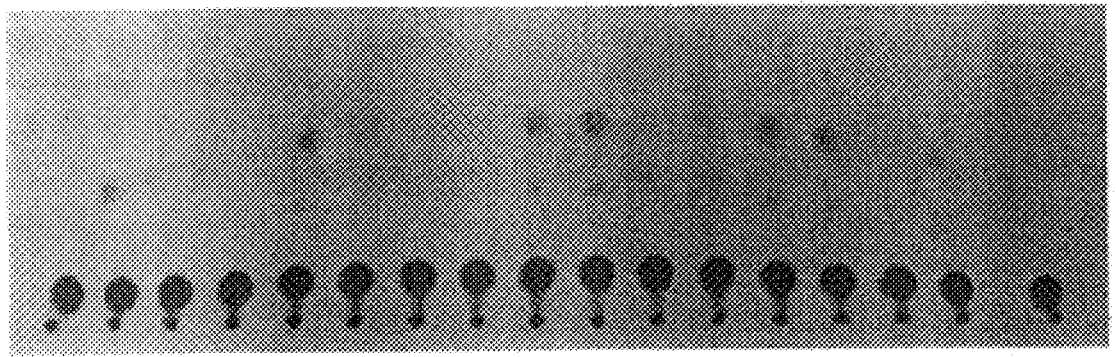
FIG._9C
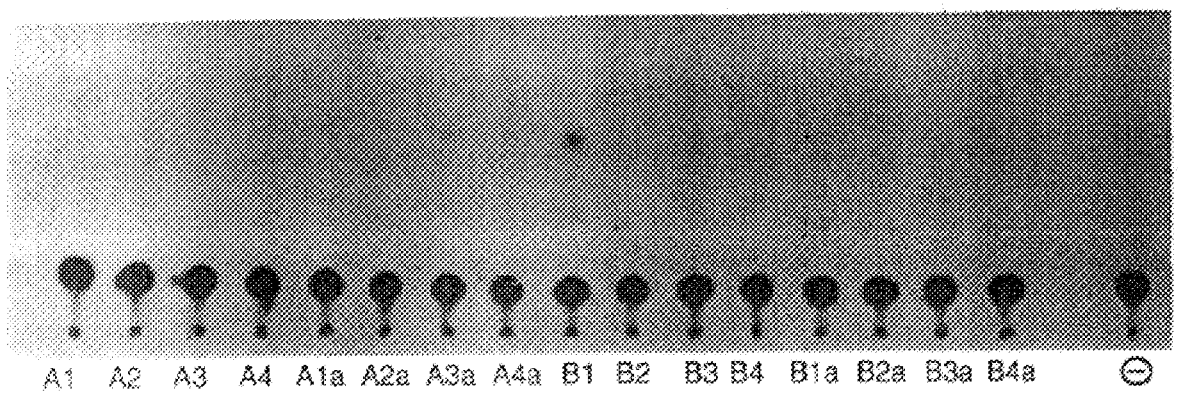
FIG._9D

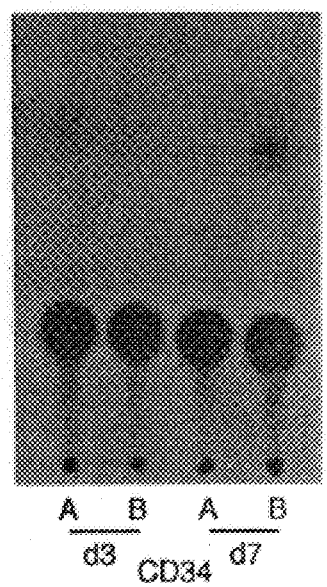
FIG._10
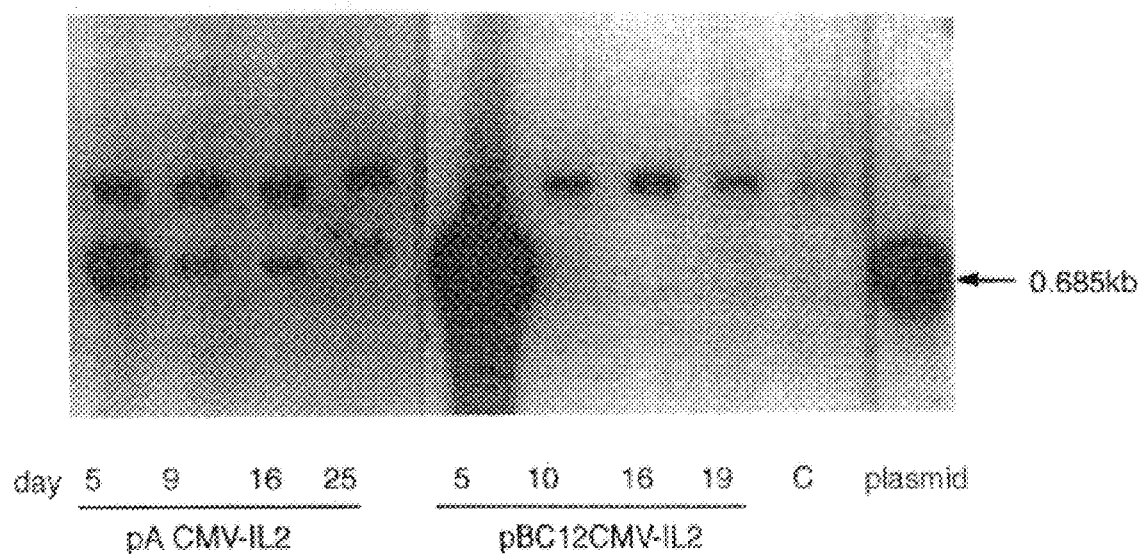
FIG._17

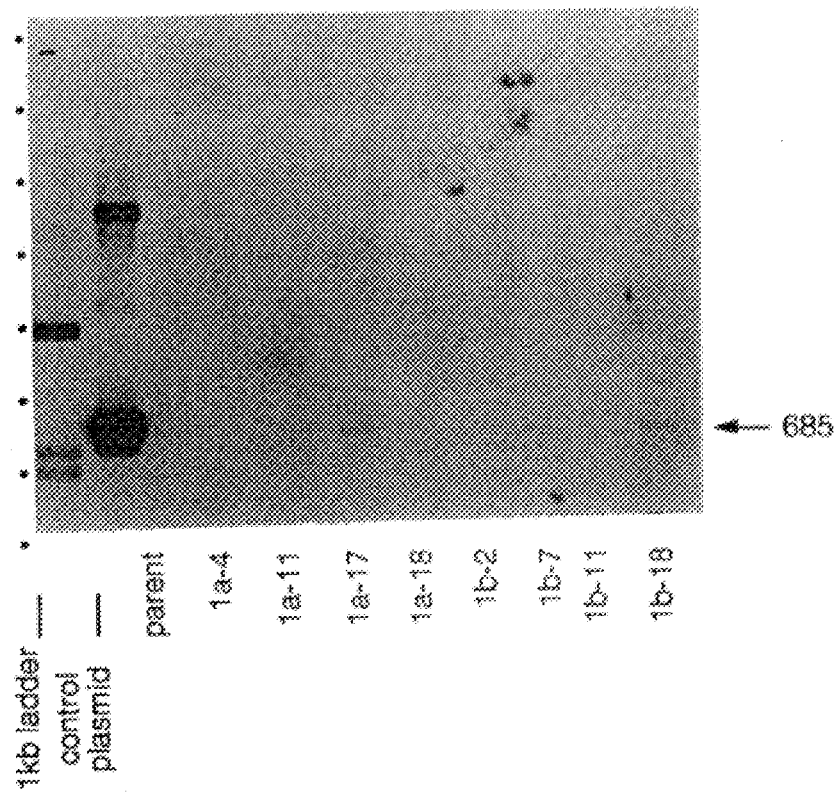
FIG._11A
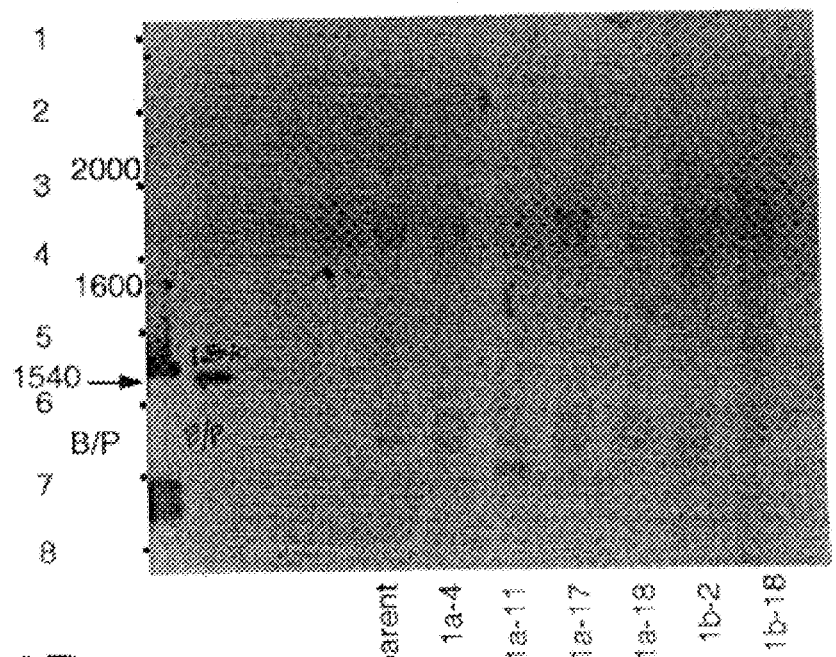
FIG._11B

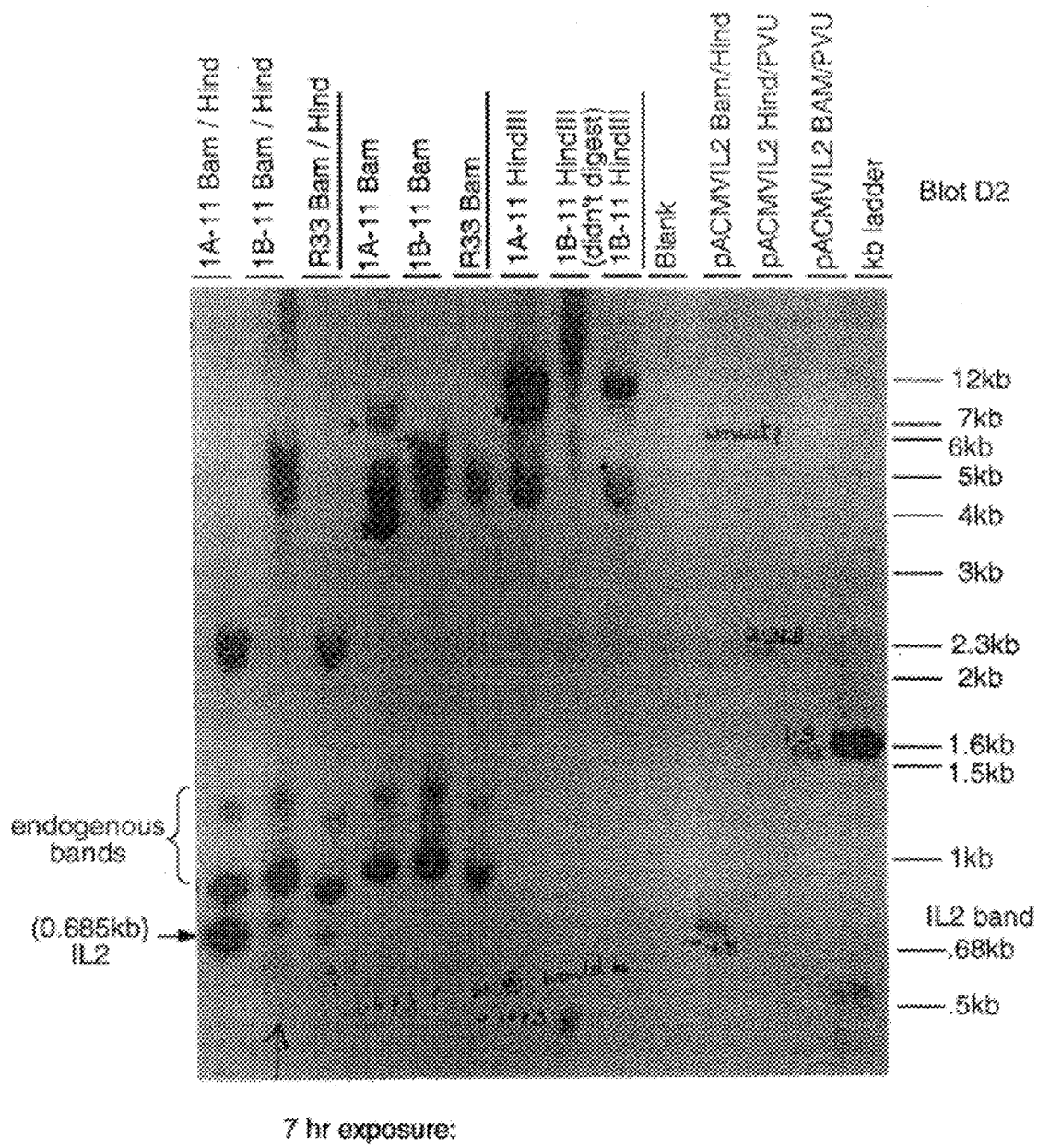
FIG._12A

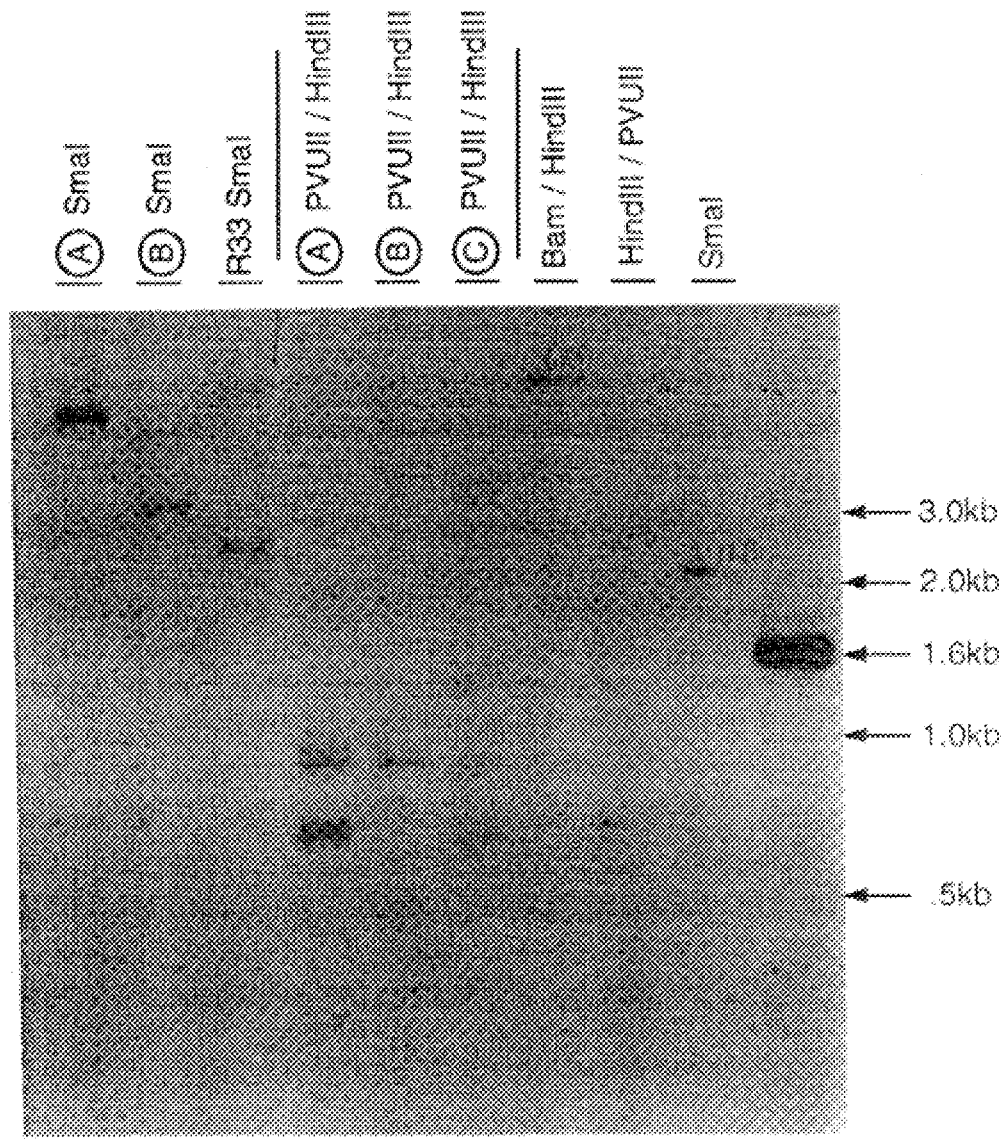
FIG._12B

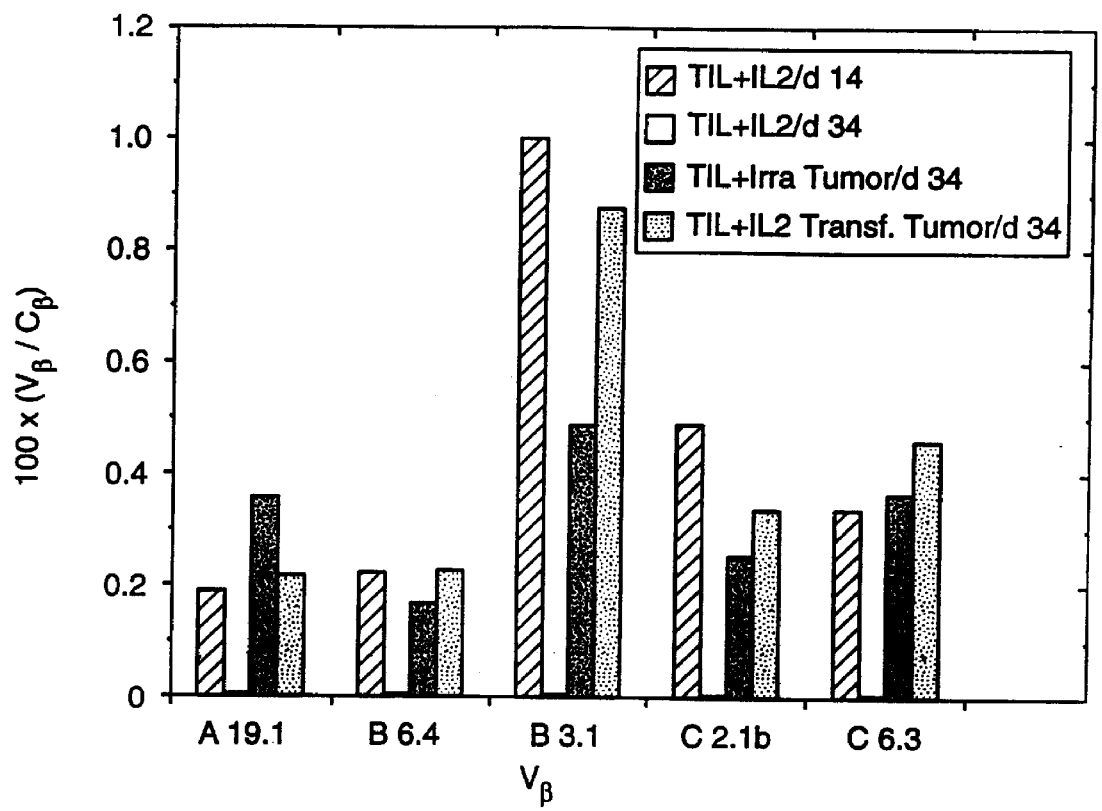
FIG._13

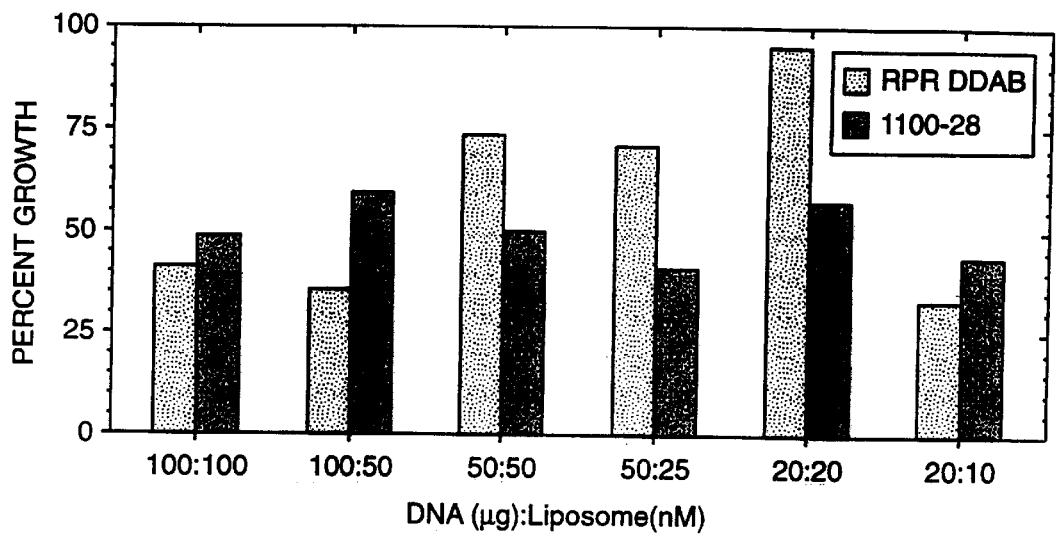
FIG._14
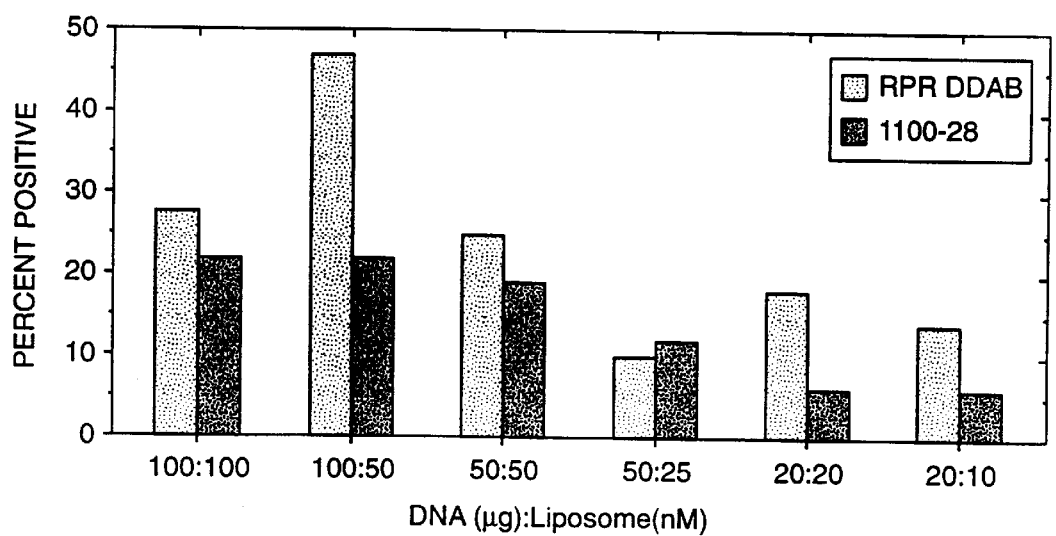
FIG._15

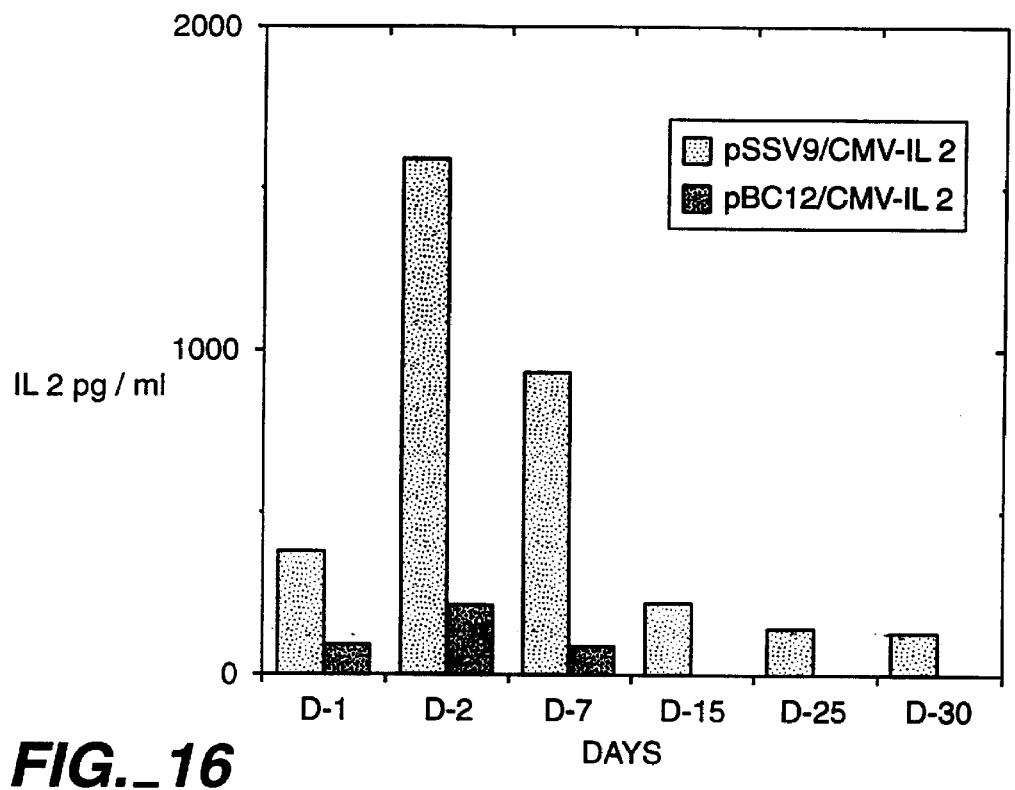
FIG._16
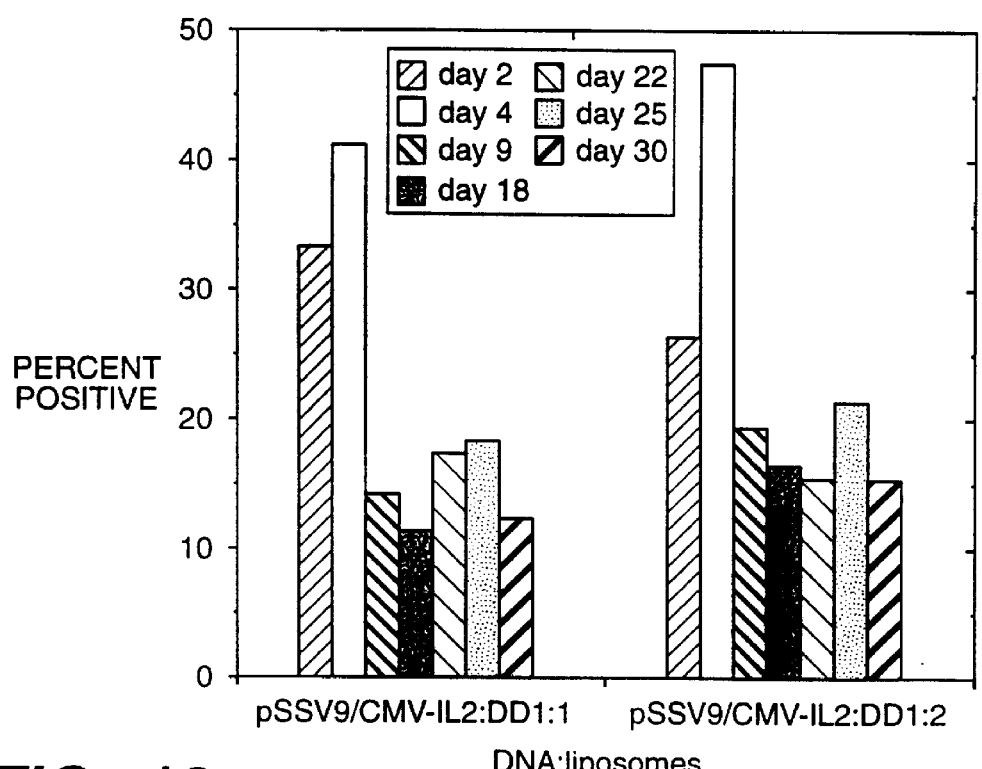
FIG._18

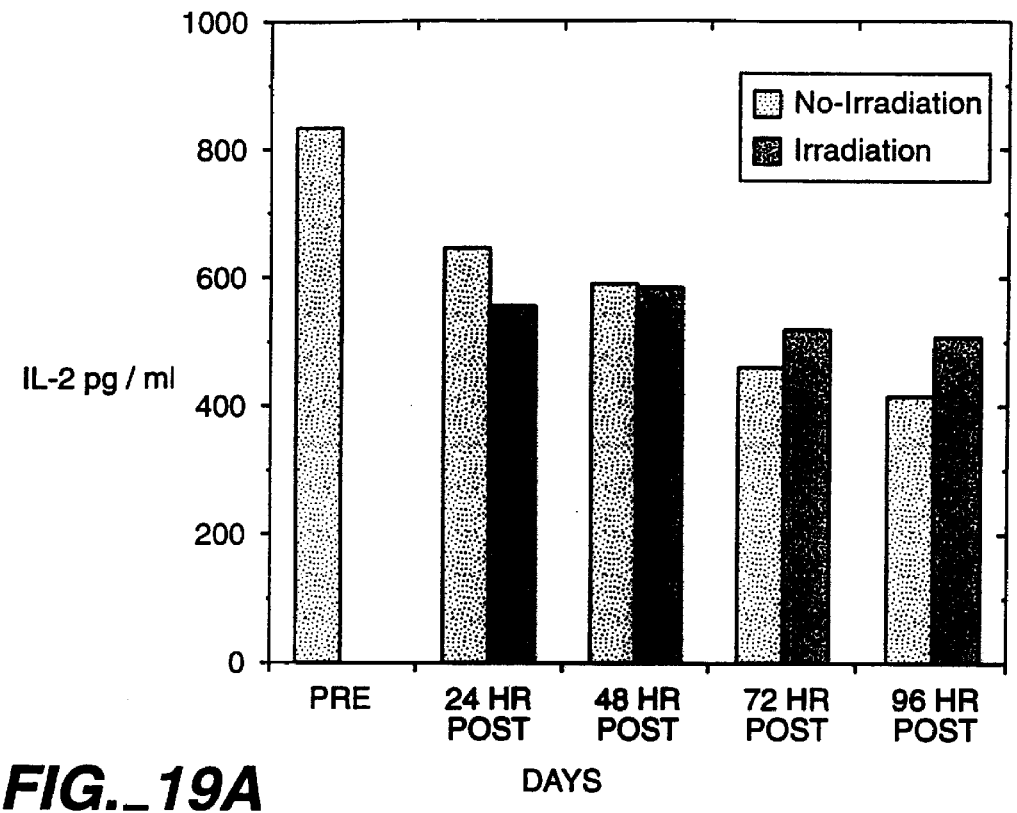
FIG._19A
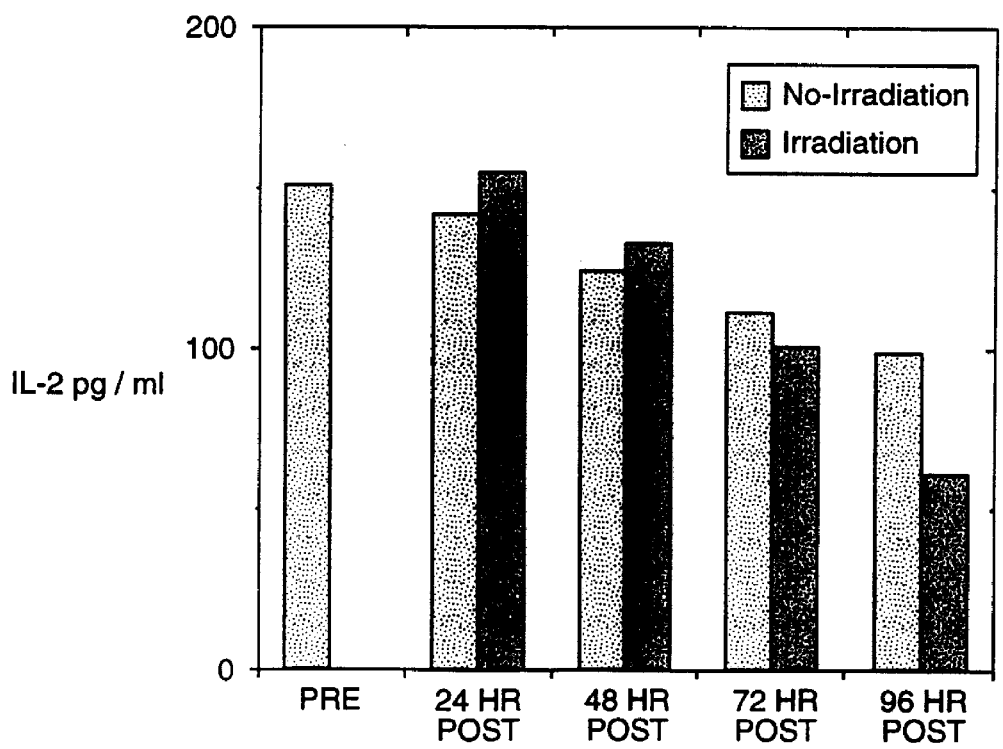
FIG._19B

ADENO-ASSOCIATED VIRAL (AAV) LIPOSOMES AND METHODS RELATED THERETO

CROSS-REFERENCE TO RELATED APPLICATIONS

This application is a Continuation-in-Part of U.S. patent application Ser. No.: 08/120,605, entitled "Adeno-Associated Viral (AAV) Liposomes and Methods Related Thereto" which was filed 13 Sep. 1993, now abandoned.

TECHNICAL FIELD

Gene Modification

The present invention involves cellular manipulation, more particularly it relates to use of cationic liposomes to facilitate transfection by adeno-associated viral (AAV) plasmids.

BACKGROUND ART

Transfection of eukaryotic cells has become an increasingly important technique for the study and development of gene therapy. Advances in gene therapy depend in large part upon the development of delivery systems capable of efficiently introducing DNA into a target cell. A number of methods have been developed for the stable or transient expression of heterologous genes in cultured cell types. These include transduction techniques which use a carrier molecule or virus.

Most gene therapy strategies have relied on transduction by transgene insertion into retroviral or DNA virus vectors. However, adenovirus and other DNA viral vectors can produce infectious sequelae, can be immunogenic after repeated administrations, and can only package a limited amount of insert DNA.

Of the viral vector systems, the recombinant adeno-associated viral (AAV) transduction system has proven to be one of the most efficient vector systems for stably and efficiently carrying genes into a variety of mammalian cell types (Lebkowski, J. S., et al., "Adeno-associated virus: A vector system for efficient introduction and integration of DNA into a variety of mammalian cell types," *Mol. Cell. Biol.* (1988) 8:3988–3996). It has been well-documented that AAV DNA integrates into cellular DNA as one to several tandem copies joined to cellular DNA through inverted terminal repeats (ITRs) of the viral DNA, and that the physical structure of integrated AAV genomes suggest that viral insertions usually appear as multiple copies with a tandem head to tail orientation via the AAV terminal repeats (Kotin, R. M., et al., "Site-specific integration of adeno-associated virus," *Proc. Natl. Acad. Sci.* (1990) 87:2211–2215). Thus, the AAV terminal repeats (ITRs) are an essential part of the AAV transduction system.

Although recombinant adeno-associated viral (AAV) vectors differ from adenoviral vectors, the transgene DNA size limitation and packaging properties are the same as with any other DNA viral vectors.

AAV is a linear single stranded DNA parvovirus, and requires co-infection by a second unrelated virus in order to achieve productive infection. AAV carries two sets of functional genes: rep genes, which are necessary for viral replication, and structural capsid protein genes (Hermonat, P. L., et al., "Genetics of adeno-associated virus: Isolation and preliminary characterization of adeno-associated type 2 mutants," *J. Virol.* (1984) 51:329–339). The rep and capsid genes of AAV can be replaced by a desired DNA fragment to generate AAV plasmid DNA. Transcomplementation of rep and capsid genes are required to create a recombinant virus stock. Upon transduction using such virus stock, the recombinant virus uncoats in the nucleus and integrates into the host genome by its molecular ends.

Although extensive progress has been made, transduction techniques suffer from variable efficiency, significant concern about possible recombination with endogenous virus, cellular toxicity and immunologic host response reactions. Thus, there is a need for non-viral DNA transfection procedures.

Liposomes have been used to encapsulate and deliver a variety of materials to cells, including nucleic acids and viral particles (Faller, D. V. and D. Baltimore, "Liposome encapsulation of retrovirus allows efficient superinfection of resistant cell lines," *J. Virol.* (1984) 49:269–272).

Preformed liposomes that contain synthetic cationic lipids have been shown to form stable complexes with polyanionic DNA (Felgner, P. L., et al., "A highly efficient, lipid-mediated DNA transfection procedure," *Proc. Natl. Acad. Sci. USA* (1987) 84:7413–7417). Cationic liposomes, liposomes comprising some cationic lipid, that contained a membrane fusion-promoting lipid dioctadecyl-dimethyl-ammonium-bromide (DDAB) have efficiently transferred heterologous genes into eukaryotic cells (Rose, J. K., et al., "A new cationic liposome reagent mediating nearly quantitative transfection of animal cells," *Biotechniques* (1991) 10:520–525). Cationic liposomes can mediate high level cellular expression of transgenes, or mRNA, by delivering them into a variety of cultured cell lines (Malone, R., et al., "Cationic liposome mediated RNA transfection," *Proc. Natl. Acad. Sci. USA* (1989) 86:6077–6081).

Ecotropic and amphotropic packaged retroviral vectors have been shown to infect cultured cells in the presence of cationic liposomes, such as Lipofectin (BRL, Gaithersburg, Md.), and in the absence of specific receptors (Innes, C. L., et al., "Cationic liposomes (Lipofectin) mediate retroviral infection in the absence of specific receptors," *J. Virol.* (1990) 64:957–961).

Even though non-viral techniques have overcome some of the problems of the viral systems, there remains a need for improved transfection efficiency in non-viral systems, a need to increase the range of cell types that are transfectable, a need to increase the duration of expression in transfected cells, and a need to increase the levels of expression following transfection. To a certain extent, improved efficiency is attained by the use of promoter enhancer elements in the plasmid DNA constructs (Philip, R., et al., "In vivo gene delivery: Efficient transfection of T lymphocytes in adult mice," *J. Biol. Chem.* (1993) 268:16087–16090).

Immune Destruction of Tumor Cells

The use of interleukin-2 (IL-2) in the treatment of neoplastic cells, such as metastatic renal cell carcinoma (RCC), is one way for carrying out immune-mediated destruction of human neoplasms. Although durable complete remissions have been achieved, the overall response rate has been low.

During testing of rIL-2 (Chiron Corp., Emeryville, Calif.) on patients with cancer, the dose limiting toxicity has been dependent upon the route and schedule of administration. High dose bolus IL-2 administration was associated with significant toxicity, a toxicity that involved nearly every organ system. Moreover, a 4% mortality rate in ECOG 0 performance status patients has been found with high dose IL-2 administration. For an overview of ECOG performance status, see, e.g., Oken, *Am. J. Clin. Oncol.* (CCT) 5:649–655 (1982) "Toxicity and Response Criteria of the Eastern Cooperative Oncology Group" Table 2, at p. 654.

As distinguished from bolus administration, use of lower dose (1–7×10⁶ Cetus units/M²/d) continuous intravenous infusion (CIV) of IL-2 has produced reports of clinical efficacy and lowered toxicity, and has suggested an improved safety profile in adoptive immunotherapy of advanced cancer (West, W. H., et al., "Constant Infusion of Recombinant Interleukin-2 in Adoptive Immunotherapy of Advanced Cancer," (1987) *N. Engl. J. Med.* 316:898).

Cellular elements which potentially improve the immune destruction of tumors when combined with IL-2 include lymphokine activated killer (LAK) cells and cytotoxic T lymphocyte (CTL) cells such as cytotoxic tumor infiltrating lymphocyte (TIL) cells.

Tumor infiltrating lymphocytes (TIL) are primarily T lymphocytes that are usually found in close apposition to a tumor mass, and which can be isolated, expanded, and activated in vitro. TIL cells are of interest in the study of neoplasia treatment because these cells have affinity for tumor cells. Accordingly, cytotoxic TIL are of articular interest since these cells have affinity for tumor and also possess cytotoxic qualities.

As a treatment methodology, TIL have been reinfused into a host along with exogenous IL-2. (see, e.g., U.S. Pat. No. 5,126,132 to Rosenberg, issued 30 Jun. 1992) Treatment with IL-2 in combination TIL has, in some instances, resulted in durable complete remissions in the treatment of advanced malignancies.

DISCLOSURE OF INVENTION

Cationic liposomes were used to facilitate adeno-associated viral (AAV) plasmid transfections of primary and cultured cell types. AAV plasmid DNA, complexed with liposomes showed several-fold higher levels of expression than complexes with standard plasmids. In addition, expression lasted for a period of 30 days without any selection. AAV plasmid:liposome complexes induced levels of transgene expression that were comparable to those obtained by recombinant AAV transduction. High level gene expression was observed in freshly isolated CD4⁺ and CD8⁺ T cells, tumor infiltrating lymphocytes, and CD34⁺ stem cells from normal human peripheral blood.

Primary breast, ovarian and lung tumor cells were transfected using the AAV plasmid DNA:liposome complexes. Transfected tumor cells were able to express transgene product after lethal irradiation. Transfection efficiency ranged from 10–50% as assessed by β-galactosidase gene expression. The ability to express transgenes in primary tumor cells is utilized to produce tumor vaccine and to produce lymphoid cells that permit highly specific modulations of the cellular immune response in cancer and AIDS, and in gene therapies.

Disclosed herein is a composition for genetic manipulation. The composition comprises a liposome comprising lipid material and adeno-associated viral material, the adeno-associated viral material can be a plasmid, and the plasmid can be pMP6-IL2 or pACMV-IL2. The adeno-associated viral material can comprise an inverted terminal repeat, or two or more inverted terminal repeats. Where two inverted terminal repeats are present in the adeno-associated viral material, a genetic material of interest can be integrated between two inverted terminal repeats; moreover, a promoter can be integrated between two inverted terminal repeats, the promoter can be a CMV immediate-early promoter, a CMV immediate-late promoter, a CMV early promoter, an ADA promoter, or a TK promoter. The composition can comprise a genetic sequence of interest, such as a genetic sequence of an IL-2 gene or a β-gal gene. The lipid material can comprise a cationic lipid. Disclosed are cells transfected by the composition.

Disclosed herein is a method for introducing a genetic sequence of interest into a host cell. The method comprises steps of providing a composition comprising liposome adeno-associated viral material and a genetic sequence of interest and contacting the composition with a host cell which comprises genetic material whereby the genetic sequence of interest is introduced into the host cell. The host cell can be a CD34⁺ stem cell; a T-cell, such as a CD3⁺, CD4⁺, or CD8⁺ cell; a cell of a tumor cell line such as a bladder, prostate, B lymphoma, or an embryonic kidney cell line; or a primary tumor cell. The step of providing a composition can comprise providing a liposome that itself comprises cationic lipid. The step of providing a composition can provide adeno-associated viral material that comprises a plasmid, and the plasmid can be pMP6-IL2 or pACMV-IL2. The method for introducing the genetic sequence of interest into a cell can further comprise a step of integrating the genetic material of interest into the genetic material of the host cell.

Disclosed is a method for treating a human patient. The treatment method comprises providing a patient with a condition; and providing a composition comprising liposome adeno-associated viral material and a genetic sequence of interest. The method further comprises a step of contacting the composition with a host cell, whereby the genetic sequence of interest is introduced into the host cell. The contacting step can be in vivo and the host cell is a cell of the patient. Alternatively, the contacting can be ex vivo, if the contacting is ex vivo the method further comprises a step of delivering the host cell comprising the introduced genetic sequence of interest to the patient. The step of providing a patient can provide a patient with a condition such as a neoplasm; an infection, such as HIV infection; an auto-immune condition; or a genetic abnormality, such as a missing or defective gene. The step of providing a composition can provide a genetic sequence of interest which encodes a peptide, an anti-sense oligonucleotide, or RNA. The step of providing a composition can provide a plasmid such as pMP6-IL2, or pACMV-IL2. The step of providing a composition can provide a genetic sequence of interest which comprises a genetic sequence encoding a cytokine, a costimulatory factor, a MHC class I molecule, a tumor-specific antigen, or a tumor-associated antigen. The step of providing a patient can provide a patient with a malignant neoplastic condition, or an HIV infection; the step of providing a composition can provide a genetic sequence of interest which comprises IL-2 genomic material to such patients. The step of providing a patient can provide a patient with a malignant neoplastic condition; the step of providing a composition can provide a genetic sequence which comprises the MDR I gene, for such patients. The step of contacting the composition with a host cell can comprise contacting with a host cell that is a neoplastic cell, a bone marrow hematopoietic cell or a peripheral blood cell; the contacting step can comprise contacting with a host cell that is a tumor infiltrating lymphocyte, a cell of a tumor cell line, or a primary tumor cell.

Disclosed is an expression vector which comprises a genetic sequence essentially that of which is depicted in FIG. 3; disclosed is an expression vector which comprises a genetic sequence substantially that of the genetic sequence of FIG. 3; and disclosed is an expression vector which comprises a genetic sequence which is that of the genetic sequence in FIG. 3. Disclosed is a cell that is gene modified with the expression vector comprising a genetic sequence essentially that of the genetic sequence in FIG. 3; the cell can be a peripheral blood cell, a bone marrow cell, a tumor infiltrating lymphocyte, a tumor cell line cell, or a primary tumor cell.

Disclosed is an expression vector comprising a genetic sequence essentially that of the genetic sequence of plasmid pMP6; an expression vector comprising a genetic sequence substantially that of the genetic sequence of plasmid pMP6; an expression vector having a genetic sequence which is that of the genetic sequence of plasmid pMP6. An expression vector comprising a genetic sequence essentially that of genetic sequence of plasmid pMP6 can further comprise a genetic sequence of interest; a cell can be gene modified with such an expression vector, the cell can be a peripheral blood cell, a bone marrow cell, a tumor infiltrating lymphocyte, a tumor cell line cell, or a primary tumor cell.

Disclosed is a method for producing a protein. The protein production method comprises steps of providing a composition comprising liposome, adeno-associated viral material and a genetic sequence of interest. The composition is contacted with a host cell which comprises genetic material, whereby the genetic sequence of interest is introduced into the host cell. The production method further comprises a step of expressing a protein encoded by the genetic sequence of interest. The host cell can be a $CD34^+$ stem cell, a T-cell, a cell of a tumor cell line, or a primary tumor cell; the host cell can be a tumor infiltrating lymphocyte, $CD3^+$, $CD4^+$, or $CD8^+$ cell. The host cell can be from a tumor cell line which is a bladder, prostate, a B lymphoma, or an embryonic kidney cell line. The step of providing a composition comprising liposome can comprise providing a composition which comprises cationic lipid. The step of providing a composition can provide adeno-associated viral material which comprises a plasmid, such as pMP6-IL2 or pACMV-IL2. The method for producing a protein can comprise a further step of integrating the genetic material of interest into the genetic material of the host cell. The step of expressing a protein can comprise expressing a lymphokine analog. The step of expressing a protein can express IL-2, β-galactosidase chloramphenicol-acetyl-transferase, or MDR I.

BRIEF DESCRIPTION OF DRAWINGS

FIG. 1. Plasmid maps of three plasmids used in the present studies. The plasmid pACMV-IL2 contained the CMV promoter, IL-2 cDNA and Rat preproinsulin and SV40 polyadenylation sequences identical to pBC12/CMV-IL2 plasmid, additionally pACMV-IL2 also had AAV inverted terminal repeats (ITRs) at both ends. The plasmid pA1CMVIX-CAT was constructed with CMV promoter and CAT gene inserted between the two AAV ITRs.

FIG. 2. This figure provides a detailed restriction map of the IL-2 embodiment of the pMP6 plasmid (pMP6-IL2)

FIGS. 3a–3e. This figure depicts the DNA sequence (SEQ ID No: 1), of the pMP6-IL2 plasmid. In the FIG., panels a-e depict successive portions of the sequence. Portions of the pMP6-IL2 sequence which correspond to known DNA sequences are indicated; the corresponding sequence information is listed directly beneath sequence information for the pMP6-IL2 plasmid. Unmarked sequences are from linkers.

FIGS. 4a–4b. FIG. 4a depicts the levels of gene expression induced by plasmid DNA:liposome complexes. Various IL-2 plasmid constructs were tested for their capability to induce gene expression with a rat bladder and a rat prostate cell line, when the constructs were complexed with liposomes. In both cell lines, the AAV plasmid construct showed the highest level of expression. The levels are expressed as picogram per ml per $10^6$ cells. FIG. 4b depicts the time-course of gene expression induced by AAV plasmid:liposome complexes. To compare the duration of transgene expression, the prostate cell line was transfected with the AAV plasmid (pACMV-IL2) and the corresponding control plasmid (pBC12/CMV-IL2) complexed with liposomes. Supernatants were collected at various time points and assayed for IL-2 levels using an ELISA. IL-2 levels are expressed as picogram/ml/$10^6$ cells in 24 hrs of culture.

FIGS. 5a–5b. A comparison of AAV plasmid:liposome complex mediated transfection to recombinant AAV transduction. To determine whether the levels of gene expression induced by AAV plasmid:liposome complexes were equivalent to rAAV transduction, the prostate cell line (FIG. 5a) and bladder line (FIG. 5b) were used to compare the transfection and transduction of IL-2 gene. IL-2 levels were assessed using an ELISA. The levels are expressed as picogram/ml/$10^6$ cells in 24 hrs of culture.

FIG. 6. Expression of IL-2 gene by lipofection with AAV plasmid:liposome complexes of various primary tumor cells. One lung, one ovarian, and two breast tumor samples were isolated from fresh tumor biopsies. IL-2 levels were measured using an ELISA. The levels are indicated as picogram/ml/$10^6$ cells in 24 hrs of culture.

FIGS. 7a–7b. Expression of IL-2 by cells transfected in accordance with the invention, then subjected to lethal irradiation. To determine the effect of irradiation on gene expression, the prostate cell line (FIG. 7a) and primary breast cells (FIG. 7b) were transfected and assessed for gene expression after lethal irradiation, as described herein. Supernatants were collected 24, 48, 72 and 96 hrs after irradiation and tested for IL-2 levels. IL-2 levels are expressed as pg/ml/$10^6$ cells in 24 hr culture.

FIG. 8. Efficiency of AAV:liposome transfection as measured by β-gal gene expression. The β-gal reporter gene was used to assess the transfection efficiency on a per cell basis. The prostate cell line was used for transfection, as described herein. The data is represented as percent of cells positive for fluorescence.

FIGS. 9a–9d. Thin layer chromatography studies depicting transfected T lymphocytes. Blood was obtained from donors referred to as A or B. Donor's A or B peripheral blood was used to isolate T cells, and for transfection. Primary T cells freshly isolated from a donor's peripheral blood were tested for transgene expression using AAV plasmid DNA:liposome complexes. T lymphocytes were fractionated as $CD3^+$ (FIG. 9a), or $CD5/8^+$ (FIG. 9b), or as $CD4^+$ (FIG. 9c) or $CD8^+$ (FIG. 9d) populations using AIS MicroCELLector devices. The relevant cells were captured and cultured as described herein. Thereafter, 5–10×$10^6$ cells were plated and transfected with 50 micrograms of AAV plasmid DNA and 50 or 100 nmoles of liposomes to obtain 1:1 or 1:2 DNA:liposome ratios. The cells were harvested 3 days after transfection. Normalized protein content from the extracts were assayed for CAT activity using a chromatographic assay.

FIG. 10. Thin layer chromatography of peripheral blood $CD34^+$ stem cells transfected with AAV plasmid:liposomes. The cells were harvested on Day 3 and Day 7 after transfection. Normalized protein content from the extracts were assayed for CAT activity using a chromatographic assay.

FIGS. 11a–11b. Enhanced chemiluminescence (ECL) Southern analysis of genomic DNA from clones transfected with AAV plasmid DNA:liposome complexes. In FIG. 11a, samples were digested with Bam HI and Hind III and probed with IL-2. For the data in FIG. 11b, samples were digested with Bam HI and probed with IL-2. All clones analyzed show presence of IL-2 gene, as demonstrated by the 0.685 kb bands. For FIG. 11a–b:
lane 1: 1 kb ladder
lane 2: plasmid cut with Bam HI/HindIII (9a) and BamHI/pvuII (9b).
lane 3: R33 untransfected
lanes 4–11: clones FIGS. 12a–12b. Southern analysis ($^{32}$P) of clone 1A11 and 1B11. After Southern blotting, the filter depicted in FIG. 12a was probed with a 0.68 kb IL2 Bam HI/Hind III fragment of pACMV-IL-2. For FIG. 12a:
lane 1: clone 1A11 cut with Bam HI/Hind III
lane 2: clone 1B11 cut with Bam HI/Hind III
lane 3: clone R33 cut with Bam HI/Hind III
lane 4: clone 1A11 cut with Bam HI
lane 5: clone 1B11 cut with Bam HI
lane 6: clone R33 cut with Bam HI
lane 7: clone 1A11 cut with Hind III
lane 8: clone 1B11 cut with Hind III
lane 9: clone R33 cut with Hind III
lane 10: left empty
lane 11: pACMV-IL2 plasmid cut with Bam HI/Hind III
lane 12: pACMV-IL2 plasmid cut with Hind III/pvuII
lane 13: pACMV-IL2 plasmid cut with Bam HI/pvuII
For the data shown in FIG. 12b, the filter was probed with a 0.85 kb pvuII/HindIII (AAV ITR/CMV) fragment of the plasmid pACMV-IL2. For FIG. 12b:
lane 1: clone 1A11 cut with smaI
lane 2: clone 1B11 cut with smaI
lane 3: clone R33 cut with smaI
lane 4: clone 1A11 cut with pvuII/Hind III
lane 5: clone 1B11, cut with pvuII/Hind III
lane 6: clone R33, cut with pvuII/Hind III
lane 7: pACMV-IL2, cut with Bam HI/Hind III
lane 8: pACMV-IL2, cut with Hind III/pvuII
lane 9: pACMV-IL2, cut with smaI
lane 10: 1 kb ladder FIG. 13. This figure depicts T Cell Receptor (TCR) repertoire analysis with RNAase protection of breast cancer TIL expanded with autologous tumor, with IL-2 transduced tumor, and with IL-2 alone. For the axes in the FIG., $V_\beta$ is a variable segment of the β chain of the TCR; $C_\beta$ is the constant segment of the β chain of the TCR; on the horizontal axis A, B, and C represent different patients.

FIG. 14. This figure depicts the proliferation of breast cancer tumor infiltrating lymphocytes (TIL); the data was obtained 5 days following IL-2 gene transfection.

FIG. 15. This figure depicts the efficiency of gene expression in breast cancer TIL transfected with the pMP6 plasmid containing the neomycin resistance gene and the Thy 1.2 gene (pMP6/neo/Thy1.2) instead of the gene for IL-2. The pMP6/neo/Thy1.2 plasmid was complexed to DDAB:DOPE liposomes. The liposome compositions were the same compositions as those for the data corresponding to FIG. 14.

FIG. 16. This figure compares the level and duration of transgene expression following transfections with various plasmid constructs. The prostate tumor cell line R3327 was transfected with standard plasmid (pBC12/CMV-IL2) or plasmid (pACMV-IL2) complexed to DDAB:DOPE liposomes. Supernatants were collected at various time points and assayed by ELISA for IL-2 levels. IL-2 levels are expressed as pg/ml/$10^6$ cells in 24 hrs of culture.

FIG. 17. This figure depicts Southern blot analysis of chromosomal DNA from R3327 cells transfected with either the AAV plasmid (pACMV-IL2) or the standard plasmid (pBC12/CMV-IL2). The blot was probed with the 0.685 kb Bam HI/Hind III fragment of the IL-2 gene. C=DNA from untransfected cells. The IL-2 insert is shown in the last lane.

FIG. 18. The figure depicts results of an intracellular assay of the transfection efficiency of the IL-2 gene in prostate cell line R3327. The cells were transfected with AAV IL-2 plasmid complexed with DDAB:DOPE liposomes, 1:1 or 1:2 composition. Transfected cells were stained at various time points for intracellular IL-2 protein levels. The data is represented as percent positive cells expressing IL-2 protein. Untransfected cells were used as negative controls and the values of controls were subtracted from the values of transfected groups.

FIGS. 19a–19b. This figure depicts expression of IL-2 by irradiated prostate tumor cell line cells (FIG. 19a) and by irradiated primary breast tumor (FIG. 19b). Primary breast cells and prostate cell line cells were transfected and assessed for gene expression post lethal irradiation. Supernatants were collected 24, 48, 72 and 96 hrs after irradiation and tested for IL-2 levels. IL-2 levels are expressed as pg/ml/$10^6$ cells in 24 hr culture.

MODES FOR CARRYING OUT THE INVENTION

The studies, disclosed for the first time herein, examined the transportation into cells of AAV plasmid DNA by a system that did not involve viral transduction. Alternatively, a method in accordance with the present disclosure efficiently transfected several mammalian cell types by use of liposomes comprising AAV material. The present disclosure relates to transfection, and utilizes the elegant carrier system of lipofection together with the proficient transduction capability of the AAV plasmid construct. Advantageously, cationic liposomes were used as a means to facilitate the entry of AAV plasmid DNA into cells in the absence of rep and capsid transcomplementation, recombinant virus or wild type AAV. A lipofection method in accordance with the invention was evaluated to assess the efficiency of gene expression. The present data established the ability to transfect unmodified stem cells, unmodified primary lymphoid cells such as T cells, a variety of freshly isolated tumor cells, and cultured mammalian cell types, with high efficiency for both transient and sustained expression of DNA. The ability to efficiently transfect unmodified T cells, such as tumor infiltrating lymphocytes; unmodified stem cells; tumor cell line cells; and, primary tumor cells is disclosed for the first time in the art.

I. Source Materials and Methods Employed

A. Cell Lines. A rat prostate cell line (R3327) and rat bladder cell line (MBT-2) were obtained from Dr. Eli Gilboa, Duke University. Both cell lines were maintained in RPMI-1640 medium supplemented with 5% fetal bovine serum (FBS). Cell line 293 is a human embryonic kidney cell line that was transformed by adenovirus type 5, and was obtained from the ATCC (Graham, F. L., et al., "Characteristics of a human cell line transformed by DNA from human adenovirus type 5," J. Gen. Virol. (1977) 36:59–72). Cell line 293 was grown in Dulbecco modified eagle medium supplemented with 10% FBS.

B. Cell preparation of Primary Tumor Cells. Primary lung, ovarian and three breast tumor cells were obtained from solid tumors of patients. The tumor samples were minced into small pieces and digested in 200 ml of AIM V medium (Gibco), supplemented with 450 u/ml collagenase IV (Sigma), 10.8K units/ml DNase I (Sigma), and 2000 u/ml hyaluronidase V (Sigma) (Topolian, S. L., et al., "Expansion of human tumor infiltrating lymphocytes for use in immunotherapy trials," *J. Immunol. Methods* (1987) 102:127–141). After 1–2 hours of digestion, cells were homogenized with a glass homogenizer (Bellco). The cells were washed three times in DPBS-CMF (Whittaker). Lymphocytes were separated from non-lymphoid cells by capture on an AIS MicroCELLector-CD5/8 device (AIS, Santa Clara, Calif.). Nonadherent cells (mainly tumor cells) were removed and cultured in RPMI 1640 supplemented with 2 mM L glutamine, 100 u/ml penicillin-streptomycin, and 10% FBS. Tumor cells were cultured for 2 to 4 weeks prior to transfection.

C. Preparation of Peripheral Blood Mononuclear Cells. Peripheral blood mononuclear cells (PBMCs) from healthy control patients were isolated from buffy coats (Stanford University Blood Bank, Stanford, Calif.), using Lymphoprep (Nycomed, Norway).

T cells, T cell subsets, or CD34$^+$ cells were further isolated using AIS MicroCELLectors (Applied Immune Sciences, Santa Clara, Calif.), devices comprising surfaces having covalently attached specific binding proteins (such as monoclonal antibodies) attached thereto. Briefly, PBMCs were resuspended at 15×10$^6$ cells per ml in 0.5% Gamimmune (Miles, Inc., Elkhart, Ind.) and loaded onto washed CD3, CD4, CD8, CD5/8, or CD34 AIS MicroCELLectors. After 1 hour, nonadherent cells were removed from the AIS MicroCELLectors. Complete medium, RPMI 1640 (Whittaker) containing 10% fetal bovine serum, 2 mM L-glutamine, and 100 u/ml penicillin/streptomycin was added to the adherent cells in the AIS MicroCELLectors. After 2–3 days in a 5% $CO_2$, 37° C. humidified environment, adherent cells were removed and prepared for transfection.

D. Plasmid Preparation. A first plasmid used in the present studies was (pACMV-IL2): this plasmid contained the human interleukin-2 gene (IL-2) as IL-2 cDNA, and the immediate-early promoter-enhancer element of the human cytomegalovirus (CMV), and Rat preproinsulin and SV40 polyadenylation sequences, flanked by adeno-associated virus inverted terminal repeats (ITRs) at both ends. (This plasmid available from Dr. J. Rosenblatt, UCLA, Calif.; Dr. Rosenblatt's name for the plasmid is pSSV9/CMV-IL2). A corresponding control plasmid pBC12/CMV-IL2, which was identical to pACMV-IL2 but which lacked the AAV terminal repeats, was also used (FIG. 1).

A second study plasmid, pA1CMVIX-CAT, contained the CMV immediate-early promoter enhancer sequences, and an intron derived from pOG44 (Stratagene); the bacterial CAT gene; SV40 late polyadenylation signal flanked by AAV terminal repeats in a pBR322 backbone (FIG. 1).

The plasmids pATK-βgal and pAADA-βgal contained the βgal gene linked to either the TK or ADA promoter, respectively, in an AAV plasmid backbone. (βgal plasmids provided by Dr. Eli Gilboa, Duke Univ.)

Another plasmid used in the present studies was pMP6. As shown in FIG. 2, plasmid containing IL-2 DNA (pMP6-IL2) is a double stranded circular plasmid. The pMP6-IL2 plasmid has the human interleukin-2 gene under the control of a CMV promoter and a SV40 polyadenylation signal. Between the promoter and the coding sequences of IL-2, there is an intron (derived from pOG44, Stratagene) which is understood to enhance the expression of IL-2 or any other exogenous gene placed into the plasmid. The whole expression cassette is between the left and right terminal sequences of adeno-associated virus. The pMP6-IL2 plasmid also has a Bluescript backbone; the backbone has a Col-E1 bacterial origin of replication and an ampicillin resistance gene which facilitates the propagation of this plasmid in *E. coli*.

FIGS. 3a–e depicts the DNA sequence of the pMP6-IL2 plasmid; panels a through e depict successive portions of the sequence. In the figure, portions of the pMP6-IL2 sequence which correspond to known DNA sequences are indicated; the corresponding sequence information is listed directly beneath sequence information for the pMP6-IL2 plasmid. Unmarked sequences are from linkers.

Standard plasmid constructs that contained the IL-2 gene, but that did not contain AAV components were also used. The standard plasmid constructs carried the IL-2 gene, with an adenosine deaminase (ADA), a thymidine kinase (TK) or the immediate-late cytomegalovirus (CMV) promoter (standard plasmids obtained from ATCC). Data for selected plasmids are in Table 1:

TABLE 1

Selected Plasmids Used in Present Studies

| Plasmid Name | Promoter | Genomic Elements |
|---|---|---|
| pACMV-IL2 | CMV (immediate-early) | IL2, AAV |
| pBC12/CMV-IL2 | CMV (immediate-early) | IL2 |
| pA1CMVIX-CAT | CMV (immediate-early) | CAT, AAV |
| pADA-IL2 | ADA | IL2 |
| pTK-IL2 | TK | IL2 |
| pCMV-IL2 | CMV (immediate-late) | IL2 |
| pATC-βgal | TK | βgal, AAV |
| pAADA-βgal | ADA | βgal, AAV |
| pMP6-IL2 | CMV (early) | IL2, AAV |

All plasmids were isolated by alkaline lysis and ammonium acetate precipitation, followed by treatment with DNase-free RNase, phenol/chloroform/isoamyl extractions and ammonium acetate precipitation (Ausubel, F. M., et al., *Current Protocols in Molecular Biology* (John Wiley and Sons, Inc. 1993)).

E. Liposome Preparation. Small unilamellar liposomes were prepared from the cationic lipid dioctadecyl-dimethyl-ammonium-bromide (DDAB) (Sigma) in combination with the neutral lipid dioleoyl-phosphatidyl-ethanolamine (DOPE) (Avanti Polar Lipids). Lipids were dissolved in chloroform. DDAB was mixed with DOPE in either a 1:1 or 1:2 molar ratio in a round-bottomed flask, and the lipid mixture was dried on a rotary evaporator. The lipid film was rehydrated by adding sterile double distilled water to yield a final concentration of 1 mM DDAB. This solution was sonicated in a bath sonicator (Laboratory Supplies, Hicksville, N.Y.) until clear. The liposomes were stored at 4° C. under argon. For in vivo use of liposomes via intravenous administration a DDAB:DOPE ratio of 1:4 to 1:5 is used; for intraperitoneal administration a DDAB:DOPE ratio of 1:1 to 1:2 is used.

F. Preparation of recombinant AAV (rAAV) for transduction with viral infection. For the preparation of recombinant AAV stocks, cells of the cell line 293 were split and grown to approximately 30–50% confluence. Thereupon, the cells were infected with adenovirus type 5 at a multiplicity of infection of 1 to 5, and incubated at 37° C. After 2 to 4 hours, the infected cells were cotransfected with 10 µg of a plasmid comprising a gene of interest and 10 µg of the rep capsid complementation plasmid, pABal, per 100 mm tissue culture dish (0.5–1×10$^7$ cells). Calcium phosphate coprecipitation was used for transfection (Hermonat, P. L. and Muzyczka, N., "Use of adeno-associated virus as a mammalian DNA cloning vector. Transduction of neomycin resistance into mammalian tissue culture cells," *Proc. Natl. Acad. Sci. USA* (1984) 81:6466–6470). At 12 to 18 hours after transfection, the medium was removed from the cells and replaced with 5 ml of DMEM medium containing 10% FBS.

At 48 to 72 hours after transfection, AAV was harvested according to the following procedure: Cells and medium were collected together, and freeze thawed three times to lyse the cells. The suspension of cells and medium was then centrifuged to remove cellular debris, and the supernatant was incubated at 56° C. for 1 hour to inactivate adenovirus (Hermonat, P. L. and N. Muzyczka, "Use of adeno-associated virus as a mammalian DNA cloning vector. Transduction of neomycin resistance into mammalian tissue culture cells," *Proc. Natl. Acad. Sci. USA* (1984) 81:6466–6470; Tratschin, J. D., et al., "Adeno-associated virus vector for high frequency integration, expression, and rescue of genes in mammalian cells," *Mol. Cell. Biol.* (1985) 5:3251–3260). After heat inactivation, the viral supernatant was filtered through cellulose acetate filters (1.2 $\mu$m). Viral stocks were then stored at −20° C. One milliliter of AAV supernatant was used to transduce $1 \times 10^6$ cells.

G. Cellular Transfection "Lipofection". For primary tumor cells and the rat tumor cell lines (R3327 and MBT-2), $1 \times 10^6$ cells were plated in 2 ml serum-free media per well of a 6 well dish. Thereafter, 5 $\mu$g of AAV plasmid DNA was mixed with 5 nmoles of DDAB as liposomes composed of DDAB and DOPE in a 1:2 molar ratio, respectively. Serum-free media (0.5 ml) was added to the AAV:liposome complex, which was then transferred to the cells. To effect lipofection, the cells were incubated at room temperature for 5 minutes, then fetal bovine serum was added to the cells to yield a final concentration of 5% fetal bovine serum.

For T cells, $5-10 \times 10^6$ cells were plated in 1 ml of serum-free media per well of a 6 well dish. 50 $\mu$g of plasmid DNA was mixed with 50 nmoles of DDAB as liposomes composed of DDAB and DOPE in a 1:1 molar ratio. The transfections "lipofections" were then performed as for tumor cells.

For stem cells, $1-2 \times 10^6$ cells were transfected with complexes comprising 10 micrograms of plasmid DNA and 10 nmoles of liposome. The transfected cells were cultured with media containing stem cell factor, IL-3 and IL-1. On Day 3 and 7, the cells were harvested and extracts were made.

H. IL-2 Assay. Cells were counted, and $1 \times 10^6$ cells were plated in 1 ml per well of a 24 well plate. The following day, supernatants were collected and assessed by using a Quantikine IL-2 ELISA kit (R&D Systems, Minneapolis, Minn.). IL-2 levels were defined as picograms/ml of the supernatant.

I. β-galactosidase Assay. The FluoReporter lacZ gene fusion detection kit from Molecular Probes (Eugene, Oreg.) was used to quantitate lacZ β-D-galactosidase in single cells by measurement of the fluorescence of the enzyme hydrolysis product, fluorescein. The AAV/β-gal plasmids (pATK-βgal and pAADA-βgal) were used with this kit. Fluorescein is produced by enzymatic cleavage of fluorescein di-b-D-galactopyranoside (FDG) in cells that express the marker gene b-D-galactosidase. The cells then were analyzed using flow cytometry (FACScan, Becton Dickinson, San Jose, Calif.)

II. Study Results

A. Level of IL-2 gene expression by use of AAV plasmid:cationic liposome complex. To evaluate the gene transfer efficiency of AAV plasmids, the IL-2 gene transfer efficiencies of AAV plasmids were compared to the efficiencies of standard plasmid constructs. The standard plasmids carried the IL-2 gene, with an adenosine deaminase (ADA) promoter (pADA-IL2), a thymidine kinase (TK) promoter (pTKIL-2), or the immediate-late cytomegalovirus (CMV) promoter (pCMV-IL2). An AAV IL-2 study plasmid (pACMV-IL2) contained the CMV promoter (immediate early), with the IL-2 gene placed downstream of the promoter. (FIG. 1) As shown in FIG. 1, the corresponding control plasmid, the pBC12/CMV-IL2 construct, was identical to pACMV-IL2, but lacked the AAV terminal repeats (ITRs).

For comparison, five plasmids (pACMV-IL2, pBC12/CMV-IL2, pADA-IL2, pTK-IL2, pCMV-IL2,) containing the IL-2 gene were complexed with liposomes and tested for transfection efficiency on the two cultured tumor cell lines: the rat bladder (MBT-2) and the rat prostate (R3327) cell lines. The cell lines were transfected with 10 micrograms of plasmid DNA complexed to 10 nmoles of liposomes per $1 \times 10^6$ cells. Supernatants were collected on Day 3 and tested for the levels of IL-2 using an IL-2 ELISA kit.

The AAV plasmid (pACMV-IL2) induced the highest levels of expression in both cell lines (FIG. 4a). The IL-2 gene with an ADA promoter (pADA-IL2) induced the least amount of expression in both cell lines. As shown in FIG. 4a, both TK and CMV (immediate-late promoter) IL-2 constructs induced comparable levels of IL-2 expression in both cell lines. However, the pBC12/CMV-IL2 plasmid, which contained CMV immediate-early promoter showed higher levels of gene expression in the prostate cell line when compared to the bladder cell line. Among the plasmids tested, the AAV IL-2 study plasmid induced the highest level of expression in both cell lines, with a significant level of increase observed in the prostate cell line.

The durations of expression induced by the corresponding control plasmid (pBC12/CMV-IL2) and the AAV IL-2 study plasmid (pACMV-IL2) in the prostate cell line R3327 were studied (FIG. 4b). Expression was assessed up to 30 days in these cultures without any selection. The cells were seeded at $1 \times 10^6$/ml and supernatants were collected for analysis every 24 hours. The cells doubled every 48 hours in culture. The data in FIG. 4b indicate that, in addition to the enhanced levels of expression, the duration of expression lasted 30 days post-transfection with AAV plasmid (pACMV-IL2). Notably, significant expression continued throughout the full duration of the time period of evaluation. As shown in FIG. 4b, both plasmids induced maximum levels of expression between Day 2 and Day 7, by Day 15 IL-2 levels declined and then were maintained at approximately 100 pg/ml only in the AAV plasmid transfected group. Similar, sustained levels of expression were observed in the bladder cell line, as well as with cells from primary lung, breast and ovarian tumor, when AAV plasmid:liposome complexes were used for transfection (data not illustrated in FIG. 4b).

B. Comparison of AAV Plasmid:liposome transfection "lipofection" and recombinant AAV transduction. The prostate and bladder cell lines were transfected and transduced, to determine whether optimal AAV:liposome transfection was comparable to optimal recombinant AAV transduction. For optimal transfection, 10 micrograms of AAV plasmid DNA was complexed to 10 nmoles of liposomes per $1 \times 10^6$ cells in 2 ml final volume. For maximal rAAV transduction, 2 ml of the viral supernatant was added to $1 \times 10^6$ cells in 1 ml of complete media. After 24 hrs, the cells were washed and resuspended in fresh complete media. Supernatant was collected at various time points after transfection and transduction.

In the prostate line (FIG. 5a), transfection induced higher levels of expression than AAV transduction under test conditions (2 ml of viral supernatant for $1 \times 10^6$ cells, versus 10 $\mu$g DNA:10 nmoles of liposomes). Although results on Day 3 through Day 5 showed approximately 10-fold higher levels of IL-2 with transfection, by Day 20 comparable levels were observed in both transfected and transduced groups.

Transduction with recombinant AAV initially induced higher levels of IL-2 production in the bladder cell line, as compared to transfection using liposomes (FIG. 5b). Similar to the prostate cell line, transduction of the bladder cell line also showed a decline in IL-2 levels by Day 20, although IL-2 levels from transfection increased during this period; comparable levels of IL-2 were produced through Day 33 in both transfected and transduced groups.

C. Transfection of primary tumor cells using AAV plasmid DNA:liposome complexes. In the foregoing experiments disclosed herein, significant transgene expression was demonstrated in cultured cell lines. In order to assess whether cationic liposome:AAV plasmid DNA complexes also mediated comparable transgene expression in freshly isolated primary tumor cells, cells of four different primary tumors were transfected with AAV IL-2 study plasmid using liposomes. Tumor cells were cultured in RPMI-1640 media supplemented with 10% FBS for 2–3 weeks prior to the transfection. The cells were plated to $1 \times 10^6$ cells per ml concentration and transfected with 10 micrograms of DNA complexed with 10 nmoles of liposomes. Supernatants were collected on Day 2 and 3.

As shown in FIG. 6, all four primary cell types produced significant levels of IL-2 after transfection. The highest level of expression was observed on Day 3 during the 10 Day study period (lung and one breast sample were studied for longer periods). IL-2 gene expression was followed in cells of the lung tumor and in cells of one of the breast tumors as long as 25 days after transfection in culture. The levels on Day 15 were equivalent (100 pg/ml IL-2) in both cell lines, and in the cells derived from primary tumors. (data not shown).

D. Effect of lethal irradiation on transgene expression. To determine the effect of irradiation on gene expression, the prostate cell line (FIG. 7a) and cells of a primary breast tumor (FIG. 7b) were transfected and assessed for gene expression after lethal irradiation. Both cell types were transfected using optimal AAV plasmid:liposome complexes. On the second day after transfection, an aliquot of each culture was subjected to 6000 rad using $^{60}$Co irradiator, whereby cellular division is abolished, and the aliquots were then kept in culture. One-half of each culture was maintained as a non-irradiated control. The aliquots were subjected to 6000 rad using a $^{60}$CO irradiator, while the expression level of IL-2 was approximately 300–400 pg/ml. Supernatants were collected 24, 48, 72 and 96 hrs after irradiation, and then tested for IL-2 levels.

As shown in FIGS. 7a–b, lethal irradiation post-transfection did not inhibit transgene expression. Neither the prostate cell line nor the primary tumor cells exhibited any change in IL-2 expression after irradiation. Thus, although cellular division was abolished, IL-2 secretion was not sensitive to irradiation. This is advantageous, since many gene therapy strategies involve gene delivery to primary T lymphocytes (which do not generally divide absent activation) and often cannot be transduced via viral infection.

E. Level of β-D-galactosidase gene expression by use of AAV plasmid:liposome complex. To demonstrate the expression levels on a per cell basis, the β-D-galactosidase gene was used for transfection experiments. Each of two AAV β-gal plasmids (pATK-Bgal and pAADA-Bgal) (plasmids obtained from Dr. Eli Gilboa, Duke University) were complexed with cationic liposomes and used for transfection of the prostate cell line. Ten micrograms of pATK-βgal or pAADA-βgal plasmid DNA was complexed with 10 nmoles of liposomes, the complexes were then used to transfect $1 \times 10^6$ cells in 2 ml volume. At various time points, approximately $5 \times 10^5$ cells were harvested and stained with fluorescent substrate FDG and analyzed using flow cytometry.

Maximum transgene expression was observed between Day 7 and Day 15 (FIG. 8). Significant levels of β-gal activity were observed through Day 25. Flow cytometry analysis of β-gal positive cells showed maximal levels of 10 to 50% transfection efficiency with both plasmid constructs. The levels declined to 5 to 10% by Day 25. The expression pattern and duration was similar to that of IL-2 expression set forth above.

F. Transgene expression induced by AAV plasmid:liposome complex in freshly isolated peripheral blood T cell subpopulations. The effect of AAV plasmid:liposome complex in transfecting freshly isolated human peripheral blood T cell populations was examined. The gene for chloramphenicol acetyl transferase (CAT) enzyme was used as the reporter gene in the pA1CMVIX-CAT plasmid (FIG. 1). The pA1CMVIX-CAT constructs were made using the AAV backbone (pA1) with CMV immediate-early promoter enhancer sequences and CAT gene. Total and purified $CD4^+$ and $CD8^+$ subpopulations of T cells were used for transfections. Both total (CD3 or CD5/8 selected) and purified (CD4 or CD8 selected) subpopulations of T cells (FIGS. 9a–d), as well as $CD34^+$ stem cells (FIG. 10, described in Section G. below), showed significant levels of CAT gene expression.

Primary T cells freshly isolated from peripheral blood were tested for transgene expression using AAV plasmid DNA:liposome complexes. Results of thin layer chromatography assays for CAT activity from $CD3^+$ T cells, CD5/8 selected T cells (total T cells), the $CD4^+$ subpopulation of T cells, and the $CD8^+$ subpopulation of T cells are depicted in FIGS. 9a–d, respectively.

T lymphocytes were fractionated as $CD3^+$, or $CD5/8^+$ or $CD4^+$ or $CD8^+$ populations using AIS MicroCELLector devices. The relevant cells were captured and nonadherent cells were washed off. The adherent cells were removed from the devices after 2 days in culture with RPMI-1640 and 10% FBS. Five to $10 \times 10^6$ cells were plated and transfected with 50 micrograms of AAV plasmid DNA and 50 or 100 nmoles of liposomes to obtain 1:1 or 1:2 DNA:liposome ratios. The cells were harvested 3 days after transfection and the cell extracts normalized by protein content and CAT activity measured using a chromatographic assay. Blood was obtained from Donors referred to as A or B. Peripheral blood of Donor A or B was used to isolate the T cells, and for transfection.

As depicted in FIGS. 9a–d, the lipid composition of the liposomes comprising AAV was varied, as was the ratio of DNA to liposome. In the study of $CD3^+$ T cells (FIG. 9a) cells from one donor (Donor A) were employed. For the studies of CD5/8 selected T cells (FIG. 9b), the $CD4^+$ subpopulation of T cells (FIG. 9c), the $CD8^+$ subpopulation of T cells (FIG. 9d), and $CD34^+$ stem cells (FIG. 10), described below, cells derived from two patients (Donor A and Donor B) were utilized.

TABLE 2

Conditions Employed for Studies Depicted in FIG. 9a

| Condition Number | Parameters |
| --- | --- |
| 1. | pA1CMVIX-CAT + DDAB:DOPE (1:1), DNA:liposome ratio (1:1). |
| 2. | pA1CMVIX-CAT + DDAB:DOPE (1:1), DNA:liposome ratio (1:2). |
| 3. | pA1CMVIX-CAT + DDAB:DOPE (1:2), DNA:liposome ratio (1:1). |
| 4. | pA1CMVIX-CAT + DDAB:DOPE (1:2), DNA:liposome ratio (1:2). |

TABLE 3

Conditions Employed for Studies Depicted in FIG. 9b–d

| Condition Number | Parameters |
| --- | --- |
| 1. | pA1CMVIX-CAT + DDAB:DOPE (1:1), DNA:liposome ratio (1:1). |
| 2. | pA1CMVIX-CAT + DDAB:DOPE (1:1), DNA:liposome ratio (1:2). |
| 3. | pA1CMVIX-CAT + DDAB:chol (1:1), DNA:liposome ratio (1:1). |
| 4. | pA1CMVIX-CAT + DDAB:chol (1:1), DNA:liposome ratio (1:2). |

For the studies depicted in FIGS. 9a–d, maximum levels of expression were observed on Days 2 and 3 in both total and purified subpopulations. Significant levels of expression were detected up to Day 14. The cells were harvested 3 days after transfection, and normalized protein content from each extract was analyzed for CAT activity. The same composition of liposome, and the DNA to liposome ratio induced similar levels of expression in all the populations.

G. Transgene expression induced by AAV plasmid:liposome complex in freshly isolated CD34$^+$ stem cells. The effect of AAV plasmid:liposome complex in transfecting freshly isolated human peripheral blood CD34$^+$ stem cells was examined. The gene for chloramphenicol acetyl transferase (CAT) enzyme was used as the reporter gene in the pA1CMVIX-CAT plasmid (FIG. 1). The pA1CMVIX-CAT constructs were made, as described above. The level of CAT expression as determined by thin layer chromatography from CD34$^+$ stem cells is set forth in FIG. 10.

TABLE 4

Conditions Employed for Studies Depicted in FIG. 10

| Condition Number | Parameters |
| --- | --- |
| 1. | pA1 CMV IX CAT + DDAB:DOPE (1:1) 1:1 DNA:liposome ratio. |
| 2. | pA1 CMV IX CAT + DDAB:DOPE (1:1) 1:2 DNA:liposome ratio. |

Freshly isolated CD34$^+$ peripheral blood stem cells were transfected with AAV CAT plasmid DNA:liposome complexes. CD34$^+$ cells were purified from peripheral blood using AIS CD34 MicroCELLectors after removing essentially all the T cells using CD5/8 MicroCELLector device. The stem cells were removed from the device and 0.5–1×10$^6$ cells were transfected with complexes comprising 10 micrograms of plasmid DNA and 10 nmoles of liposome. The transfected cells were cultured with media containing stem cell factor, IL-3 and IL-1. On Day 3 and 7, the cells were harvested and extracts were made. Normalized protein content from the extract was assayed for CAT activity. As shown in FIG. 10., there were significant levels of CAT gene expression in the CD34$^+$ peripheral blood stem cells.

H. Integration Studies. FIGS. 11a–b illustrates enhanced chemiluminescence (ECL) Southern analyses of genomic DNA from stable clones (clones stable at least beyond Day 30) that were transfected with AAV plasmid DNA:liposome complexes in accordance with the invention. Genomic DNA was isolated and analyzed using the ECL direct nucleic acid labelling and detection system (Amersham). IL-2 probe was prepared from the 0.685 kb IL-2 gene from pACMV-IL2. After hybridization, the membrane was washed twice in 0.5×SSC/0.4% SDS at 55° C. for 10 minutes and twice in 2×SSC at room temperature for 5 minutes.

In FIG. 11a, samples were digested with Bam HI and Hind III and probed with IL-2. As shown in FIGS. 11a, all clones showed the presence of the IL-2 gene, as demonstrated by the 0.685 kb band in Bam HI and Hind III digested genomic DNA.

For the data in FIG. 11b, samples were digested with Bam HI and probed with IL-2. Again, all clones showed IL-2 gene integration. (FIG. 11b). In FIG. 11b, integration of IL-2 was demonstrated by the high molecular weight bands (between 1.6 and 2 kb), bands which are consistent with integration of the gene in conjunction with attached host genomic material obtained via digestion. The data in FIG. 11b indicate that there was more than one integration site, since there were multiple high molecular weight bands in the Bam HI digested genomic DNA. Furthermore, the integration site was shown to be in different locations in different clones, as demonstrated by the different size bands in the digested clones (FIG. 11b).

FIGS. 12a–b depict chromosomal DNA analyses, using a $^{32}$P Southern assay, of two clones obtained from the present study. Nuclear DNA was isolated from the two IL-2 clones (1A11 and 1B11) using the Hirt fractionation protocol. As a negative control, total DNA was isolated from untransfected cells of the R3327 cell line. After restriction enzyme digestion, 10 micrograms of each sample, along with appropriate plasmid controls, were loaded onto a 1% agarose gel, electrophoresed, denatured and transferred onto Hybond+ membrane. The filters were hybridized overnight at 68° C. with DNA fragments labelled with $^{32}$P by random priming. The membranes were then washed at 68° C. for 2×30 minutes each with 2×SSC, 0.1% SDS and 0.2×SSC, 0.1% SDS. Autoradiograms of these filters were exposed on x-ray film.

In FIG. 12a, the IL-2 gene was again used as the probe. Thus, after Southern blotting, the filter depicted in FIG. 12a was probed with a 0.68 kb IL2 Bam HI/Hind III fragment of pACMV-IL2. The data in FIG. 12a indicate that the number of copies of the IL-2 gene that integrated into a clone, varied from clone to clone; this finding was demonstrated by the various densities of the 0.685 kb band in the digests (as specified in the Brief Description of the Drawings) of cells of the two clones. Moreover, higher molecular weight bands were also demonstrated, which is consistent with integration of the IL-2 gene, together with host genomic material obtained from the various digest protocols.

For the data shown in FIG. 12b, the filter was probed with a 0.85 kb pvuII/HindIII (AAV ITR/CMV) fragment of the plasmid pACMV-IL2. The data in FIG. 12b indicate the presence of the right AAV ITR, as demonstrated by the 0.8 kb band in the smaI and pvuII digested chromosomal DNA. The presence of the left AAV ITR in one clone (clone A) was demonstrated by the 2.1 kb band in the smaI and pvuII digested chromosomal DNA.

III. Examples

A method in accordance with the invention, utilizing liposomes that comprise AAV viral material, is used to deliver genes for cytokines, costimulatory molecules such as B7, and molecules having MHC class I antigens into a wide variety of cell types. For example, such genomic material can be delivered into primary tumor cells or tumor cell lines to provide tumor vaccines; into peripheral blood or bone marrow cells to treat hematologic or neoplastic conditions.

A method in accordance with the invention, comprising use of liposomes that contain AAV viral material, is used to deliver and express genes for substances such as peptides, anti-sense oligonucleotides, and RNA. Upon expression of such peptides, anti-sense oligonucleotides and RNA, a subject's immune response is modulated. The modulation of the immune response is either that of inducing the immune response or inhibiting the immune response. Accordingly, HIV infection is treated by using anti-sense oligonucleotides, RNA, or ribozymes that have been expressed by a method in accordance with the invention. Additionally, the immunologic response to a tumor is modulated by use of peptides or RNA expressed in accordance with the invention. A patient's immune response is modulated so as to respond to tumor-specific and/or tumor-associated antigens. Accordingly, non-immunogenic tumors are modified into immunogenic tumors which induce a cytolytic T cell response, both in vivo and in vitro.

A method in accordance with the invention is used to deliver genes to primary lymphoid cells, such as B cells or T cells. An alternate method in accordance with the invention is used to deliver genetic material to $CD34^+$ stem cells. Accordingly, the genes are expressed and are used in therapy for conditions such as HIV infection, conditions of genetic defect, neoplasias, and auto-immune conditions, wherein expression of a gene of interest is desired, as is appreciated by one of ordinary skill in the art. For example, for a malignant neoplastic condition, the MDR I gene is delivered in accordance with the invention, is expressed, and has therapeutic effect.

In a further example, $CD8^+$ cells are selected with AIS MicroCELLectors. The source material for the $CD8^+$ cells is peripheral blood for HIV patients, and tumor samples for patients with neoplasia. The T cells are then activated according to methods known in the art, such as by use of phytohemagglutinin (PHA). The activated cells are grown for 20 days. Thereafter, the cells are transfected in accordance with the invention with AAV:liposome complexes comprising IL-2 genomic material. The transfected cells are returned to the patient. Thus, the subsequent administration of IL-2 to a patient in order to maintain their cytotoxic T cell activity is reduced. Advantageously, the IL-2 gene, administered in accordance with the invention, permits lessened amounts of IL-2 to be provided systemically to a patient. Reducing the amount of IL-2 that is systemically administered is advantageous, since systemically administered IL-2 is associated with lethal dose-related toxicity.

A. Tumor Vaccination

Typically, tumor vaccination protocols employ nonproliferating neoplastic cells. Proliferation of neoplastic cells is prevented by exposure of the cells to radiation, or by the cells being subjected to high pressure chambers. It is believed that when the neoplastic cells are present in the body, apart from initial tumor massings or foci, that the body is able to mount an effective antitumor response.

Some tumor vaccination trials have used gene-modified tumor (GMT) for patients with melanoma and renal cell cancer, in order to enhance tumor cell antigenicity; these trials have relied upon ex vivo retroviral gene transfer. Ex vivo retroviral gene transfer suffers from the disadvantages that it is a very complex method to perform, and that there must be active target cell division to achieve incorporation and expression of the delivered genes. Moreover, it can be very difficult to ex vivo culture sufficient neoplastic cells to provide for a suitable quantity of therapeutic product.

In contrast to retroviral gene transfer, plasmid constructs possessing the terminal repeat elements of adeno-associated virus (AAV) in locations 3' and 5' to the gene to be transduced were expressed efficiently when introduced via nonviral liposome-mediated transfer. For example, as discussed in greater detail below, liposomes were used to deliver AAV plasmid, such as pMP6-IL2, that comprised cDNA for interleukin-2 into primary human tumor cells, such as melanoma cells. The primary tumor cells then subsequently expressed interleukin-2. Tumor cell lines were also effectively transfected.

The expression of IL-2 obtained by use of AAV-liposome transfection has been durable, and of high-level. The levels of cytokine secretion from cells gene-modified by AAV plasmid-liposome compositions has exceeded the levels obtained from retrovirally infected cells.

Accordingly, cells are gene-modified by use of a composition comprising AAV plasmid and liposomes; these gene-modified cells are utilized in therapeutic tumor vaccination regimens. Advantageously, gene modification by use of a composition comprising AAV plasmid and liposomes allowed primary tumor cells to be modified, thereby obviating the general need to establish a tumor cell line from primary tumor cells in order to affect gene modification as required prior to the present disclosure. It is also highly advantageous that tumor cells that are gene-modified and express IL-2 do not need to be administered along with systemic IL-2: Systemic IL-2 is known to induce extremely serious, even fatal, side effects.

B. Lipofection of Cells with Transgene DNA for Use in Therapeutic Administration Systemic IL-2 is a current treatment for certain serious conditions such as malignant neoplasia. Additionally, activated T cells become dependent on exogenous IL-2 for the growth and survival both in vitro and in vivo. When the IL-2 stimulus is withdrawn, the T cells undergo apoptosis (DNA fragmentation) within a few days. Systemically administered IL-2 is, however, known to cause severe side effects, including death. There is a need, therefore, to develop therapies which eliminate or decrease the need for systemic IL-2 administration.

The studies represented by the following data addressed the transportation into T cells of AAV plasmid DNA and transgene DNA by a system that does not involve viral transduction. More particularly, the present data relates to transfection, and utilized the elegant carrier system of lipofection and the proficient transduction capability of AAV plasmid constructs.

Accordingly, AAV plasmids containing transgene and AAV terminal repeats were used as a DNA vector, and cationic liposomes were used as carrier molecules. (For a general discussion of transfection and expression in T lymphocytes, see, Philip, R. et al., *Mol. Cell. Biol.* (1994) 14(4):2411–2418). In a preferred embodiment, the transgene is for IL-2. AAV plasmid:liposome complexes induced levels of transgene expression comparable to levels obtained by recombinant AAV transduction. Advantageously, the cationic liposomes facilitated the entry of AAV plasmid DNA into cells in the absence of rep and capsid transcomplementation, recombinant virus or wild type AAV. The AAV plasmid DNA:liposome complexes efficiently transfected TIL cells. AAV plasmid DNA complexed with liposomes provided several-fold higher levels of expression than complexes with standard plasmids. Moreover, expression lasted for a period of 30 days without any selection.

The IL-2 gene expression system for T cells disclosed herein enables activated cells to produce sufficient endogenous IL-2 to support their maintenance in vivo; thereby apoptosis is prevented and there is no need to systemically administer IL-2.

In a controlled study, various T cell populations were transfected with an AAV plasmid, carrying IL-2 cDNA, complexed to liposomes; these populations were tested for their ability to maintain growth and proliferation without exogenous IL-2 in vitro.

For T cells, assays showed that when transfected with the IL-2 gene, primary and activated CD8+ T cells proliferated to higher levels than that of controls transfected with irrelevant gene.

Growth levels of the IL-2 transfected CD8+ cells were maintained without exogenous IL-2 and apoptosis was significantly reduced. Southern blot analysis on these transfected T cells showed the presence of the IL-2 plasmid up to 25 days. The present data demonstrated that IL-2 gene transfer into ex vivo activated and expanded CD8+ cells supported the growth of such cells, and prevented apoptosis without any exogenous IL-2.

Cells that can be gene-modified include but are not limited to: primary lung, ovarian and breast carcinoma; melanoma; autologous fibroblasts; transformed B cells; dendritic cells; and cells of cell lines. Gene-modified cells such as these can be used alone or in conjunction with tumor cells to stimulate TIL. Gene modified cells can be made to express tumor associated antigens (e.g., HER2, K-ras, mucins) of use to provide antigen presentation for TIL stimulation during culture. Moreover, antigen presenting cells, such as transformed B cells and dendritic cells, can be gene-modified and made to express tumor associated antigenic peptides such as MAGE-1 and MART-1 to provide antigen presentation for TIL stimulation during culture. The present data establishes the ability to transfect T cells and neoplastic cells with high efficiency for both transient and sustained expression of DNA. The transfection occurred in the absence of any recombinant virus (producible from rep and cap capsid particles in adenoviral infected cells). The cells obtained by AAV transfection are used to treat patients. The patients treated with such cells obtain notable therapeutic benefit.

1. Reactant Preparation and Protocols Employed
   a. Plasmids.
      i. Plasmid pACMV-IL2

Plasmid (pACMV-IL2) contains the human interleukin-2 gene (IL-2) as IL-2 cDNA, and the immediate-early promoter-enhancer element of the human cytomegalovirus (CMV), and rat preproinsulin and SV40 polyadenylation sequences, flanked by adeno-associated virus inverted terminal repeats (ITRs) at both ends. A corresponding control plasmid, pBC12/CMV-IL2, was identical to pACMV-IL2 but lacked the AAV terminal repeats. FIG. 1 depicts plasmid maps of pACMV-IL2 and pBC12/CMV-IL2.

ii. Plasmid pMP6-IL2

As shown in FIG. 2, plasmid pMP6-IL2 is a double stranded circular plasmid. The pMP6-IL2 plasmid has the human interleukin-2 gene under the control of a CMV promoter and a SV40 polyadenylation signal. Between the promoter and the coding sequences of IL-2, there is an intron which enhances the expression of IL-2. The whole expression cassette is between the left and right terminal sequences of adeno-associated virus. The pMP6-IL2 plasmid also has a Bluescript backbone; the backbone has a Col-E1 bacterial origin of replication and an ampicillin resistance gene which facilitates the propagation of this plasmid in *E. coli*.

FIGS. 3a–e depicts the DNA sequence of the pMP6-IL2 plasmid; panels a through e depict successive portions of the sequence. In the figure, portions of the pMP6-IL2 sequence which correspond to known DNA sequences are indicated; the corresponding sequence information is listed directly beneath sequence information for the pMP6-IL2 plasmid. Unmarked sequences are from linkers.

The pMP6-IL2 plasmids were purified by alkaline lysis and ammonium acetate precipitation. The concentration of nucleic acid was determined by UV absorption at 260 nm.

iii. Plasmid pA1CMVIX-CAT

Plasmid pA1CMVIX-CAT contains the CMV promoter enhancer element, the intervening splice acceptor sequences, the bacterial chloramphenicol acetyltransferase (CAT) gene and the simian virus 540 late polyadenylation signal flanked by AAV terminal repeats in a pBR 322 derivative.

Plasmids were purified by alkaline lysis and ammonium acetate precipitation. Nucleic acid concentration was measured by UV absorption at 260 nm.

b. Liposome Preparation.
      i. Liposomes used with pACMV-IL2

Small unilamellar liposomes were prepared from the cationic lipid, dioctadecyl-dimethyl-ammonium-bromide (DDAB) (Sigma), in combination with the neutral lipid, dioleoyl-phosphatidyl-ethanolamine (DOPE) (Avanti Polar Lipids). The lipids were dissolved in chloroform. DDAB was mixed with DOPE in a 1:1 molar ratio in a round-bottomed flask. The lipid mixture was dried on a rotary evaporator. The lipid film was rehydrated by adding sterile double distilled water to yield a final concentration of 1 mM DDAB. This solution was sonicated in a bath sonicator (Laboratory Supplies, Hicksville, N.Y.) until clear. The liposomes were stored at 4° C. under argon.

ii. Liposomes used with pMP6-IL2

Liposomes were prepared by combining the cationic lipid dioctadecyl-dimethyl-ammonium-bromide (DDAB) with the neutral lipid dioleoyl-phosphatidyl-ethanolamine (DOPE) in a 1:1 molar ratio; or by combining DDAB with cholesterol in a 1:0.6 molar ratio, and evaporating the lipids to dryness in a rotary evaporator. The lipids were resuspended in sterile deionized water to yield a concentration of 1 mM DDAB and then sonicated to clarity in an ultrasonic bath. Liposomes were stored under argon at 4° C.; and, were stable for at least 4 months.

iii. Liposomes Used in TIL Stimulation

Liposomes were prepared by combining the cationic lipid (DDAB) with either the neutral lipid (DOPE) or cholesterol in a 1:1 or 1:2 molar ratio and evaporating the lipids to dryness in a rotary evaporator. The lipids were resuspended in sterile deionized water to yield a concentration of 1 mM DDAB. The solution was then sonicated to clarity in an ultrasonic bath. Liposomes were stored under argon at 4° C. and were stable for at least 4 months.

c. Cell Preparation
      i. Isolation of TIL Cells

TIL cells were selected with AIS MicroCELLectors®. The source material was tumor or lymphatic system samples taken from patients with a neoplasia. The T cells were then activated according to methods known in the art, such as by use of IL-2. The activated cells were grown for 20 days.

ii. Isolation of T cells and Neoplastic Cells

Primary T cell populations were isolated from peripheral blood mononuclear cells, and TIL and tumor cells were isolated by use of subject devices (Microcellector®, Applied Immune Sciences). The cells were prepared for transfection according to standard methodologies.

1) Neoplastic Cells from a Solid Tissue Source To obtain a cell population that will be transfected, cells were obtained from solid primary or metastatic lesions, or from lymphatic system tissues. For example, biopsies of breast tumors were obtained from patients undergoing surgery with a pre-operative diagnosis of suspected refractory or recurrent breast cancer. These studies were also successfully performed with cells from ovarian tumor. The biopsy tissue cores were divided with fragments processed for routine pathology by light microscopy and immunohistochemical analysis.

Accordingly, freshly excised tumors were cut into 0.5 cm cubes. Up to 10 tumor cubes were transferred to a 25 ml spinner flask containing 25 ml of AIM V media (GIBCO). The flask was placed in an incubator at 37° C. which contains 5% $CO_2$; the flask was gently stirred at 100–120 RPM for a period of 12–18 h. After incubation, any tissue that was not disaggregated was filtered, and then cells in suspension were pelleted. The pelleted breast cancer cells were placed into tissue culture flasks (Falcon) in AIM V media. Cells were maintained in humidified air containing 5% $CO_2$, at a temperature of 37° C.

After 48 hours of culture in the serum-free media, adherent and non-adherent cell lines were generated by aspirating the non-adherent cells. The non-adherent cells were washed and then recultured in a fresh flask. During reculture, the adherent cells were grown to confluence, trypsinized with 0.05% trypsin and 0.02% EDTA, and passaged at high cell density into new flasks.

Alternatively, primary tumor cells of lung, ovarian and breast origin were obtained from solid tumor samples and isolated as follows: The tumor was minced and subjected to enzymatic digestion for 2 hours. The tissue was then homogenized and washed with PBS. Lymphocytes were separated from non-lymphoid cells by capture on AIS MicroCELLector-CD5/8 devices. The nonadherent population contained tumor cells which were cultured in RPMI 1640+10% FBS with L-glutamine and pen/strep.

2) Neoplastic Cells from a Fluid Source As an alternate source for cells that will ultimately be transfected, malignant ascites fluid or pleural effusions were used to isolate autologous neoplastic cells.

Accordingly, malignant ascitic or effusion fluid was centrifuged, and the pellet containing cells was resuspended in AIM V media. The cells were counted and the lymphocyte subpopulation was depleted either by using a 2 step Ficoll gradient or by using AIS CELLector™ CD5/CD8 devices. The choice of using the Ficoll gradient or AIS CELLector™ CD5/CD8 devices was made in view of the total cell number, as appreciated by one of ordinary skill in the art. Isolation of neoplastic cells from a fluid source is particularly relevant to malignancies such as ovarian and lung cancer which are known to correlate with pleural effusions. The T cell-depleted fraction was enhanced for neoplastic cells.

All autologous neoplastic cells were characterized by light microscopy, flow cytometry and immunohistochemical staining to assay oncogene expression and to establish a proliferation index. For example, for studies on patients with breast cancer, only cells that were morphologically breast cancer cells or that stain with breast-cancer specific antibodies were deemed autologous tumor cells, and then subsequently utilized as such.

3) Cell Lines

Cells of the murine B lymphoma cell line 38C13 were provided by Dr. Bernd Gansbacher (Sloan Kettering Memorial Cancer Center); rat prostate cell line R3327 cells were provided by Dr. Eli Gilboa (Duke University); and, MDA-231 breast tumor cell line cells were obtained from ATCC.

d. Cellular Transfection "Lipofection".

i. Lipofection of TIL Cells

For transfection of TIL cells, 5–10×$10^6$ cells were plated in 1 ml of serum-free media per well of a 6-well dish. 50 μg of plasmid DNA comprising IL-2 genomic material (e.g., pMP6-IL2) was mixed with 50 nmoles of DDAB (as the liposomes composed of DDAB and DOPE in a 1:1 molar ratio). Serum-free media (0.5 ml) was added to the AAV:liposome complex. The AAV:liposome complex and serum-free media was then placed with the cells. To affect lipofection, the cells were incubated at room temperature for 5 minutes, then fetal bovine serum was added to the cells to yield a final concentration of 5% fetal bovine serum.

The transfected TIL cells are returned to the patient. These cells provide the therapeutic benefits of cytotoxic TIL cells in combination with IL-2. Advantageously, the need to systemically administer IL-2 to a patient in order to maintain cytotoxic T cell activity is reduced or eliminated. A reduction in the amount of systemically administered IL-2 is advantageous since IL-2 administered in this manner is known to correlate with potentially lethal dose-related toxicity.

ii. Lipofection of Neoplastic Cells

A neoplastic cell culture, such as a culture of breast cancer cells or ovarian tumor cells, was transfected in the following manner: Neoplastic cells (1×$10^6$ cells) were transfected with 5 micrograms of plasmid DNA (e.g., pMP6-IL2) mixed with 30 nmoles of total lipid, wherein the lipid comprises liposomes composed of DDAB and DOPE in a 1:1 molar ratio. One ml of AIM V media was added to the liposome-DNA complex, and was incubated at room temperature for 30 minutes. The combination of the media and the liposome-DNA complex was then transferred to the cells. The cells were then incubated at 37° C. for 24 hours. After 24 hours, the cells were lethally irradiated (10,000 RADS).

Alternatively, DNA-liposome complexes were formed by the following method: The desired amount of DNA was transferred to a sterile vial and one or 2 nmole DDAB per μg DNA was added and mixed. Then, 1 ml serum free media was added to the liposome-DNA complex. All cells to be transfected were plated in six well plates. Primary tumor and tumor cell lines were plated at 1×$10^6$ cells per well in 2 ml serum-free media. The liposome-DNA complex was added to the cells and incubated for 5 min at room temperature. FBS was added to bring the final concentration to 10%.

e. Assay of Transgene Expression i. Extracellular Assays Expression of the transgene was documented by assaying IL-2 expression by the lethally irradiated cells; these IL-2 assays can be by ELISA assay, in accordance with information known to those of ordinary skill in the art.

Cell-free supernatants were collected and their IL-2 concentration was determined by ELISA at various time points. For example, IL-2 assays were performed on 72 hour supernatants, in duplicate. Successful transfection of gene-modified cells was defined as where IL-2 concentrations of >100 pg/72h/$10^6$ cells were obtained.

ii. Intracellular Assays Cells were harvested at various time points, washed with PBS and resuspended in cold 1% paraformaldehyde in PBS. After 10 minutes at 4° C., cells were washed with cold saponin buffer (0.1% saponin, 10% FBS in PBS) and stained with mouse anti-human IL-2 antibody for 15 minutes at 4° C. Cells were then washed with cold saponin buffer and stained with FITC conjugated goat anti-mouse F(ab')2 antibody for 15 min, at 4° C. Cells were washed with saponin, then PBS and analyzed by flow cytometry.

f. Southern Hybridization for IL-2 DNA

Chromosomal DNA was isolated by Hirt fractionation. After restriction digestions, 5 μg of DNA per sample was electrophoresed, transferred to Hybond N+nylon membrane and hybridized with the 0.685 kb IL-2 fragment.

g. Cytotoxicity Assay

Target cells were labelled with 100 μCi $^{51}$Cr per 1×$10^6$ cells. 5000 target cells were plated in triplicate in 96 well plates. Effector cells were added to yield a 20:1 effector to target ratio. 100 μl supernatant from each well was collected after a four hour incubation, and counted in a γ-counter.

h. Proliferation Assay

To assay proliferation, $5\times10^4$ cells in 100 μl AIM V media were plated in triplicate in 96 well plates. Each well was pulsed with 1 μCi $^3$H-thymidine. Cells were harvested 24 hours later and counted with a scintillation counter.

i. TCR Analysis

TIL cells were frozen at various time points in culture and after stimulation experiments. TCR restriction was analyzed by reverse transcriptase (RT) PCR in accordance with methodologies known in the art.

2. Resulting Data and Findings a. Ex Vivo Activation of Tumor Specific CTL; Stimulation of TIL Cells During Culture Stimulation was carried out with TIL cultured in a 50:1 ratio with autologous irradiated tumor; or with IL-2 transfected, irradiated autologous tumor. The period of stimulation was for 5–7 days. These cells were compared to TIL cultured in AIM V media supplemented with 600 IU/ml rIL-2. Cells were assayed after stimulation for changes in phenotype, cytotoxic activity, proliferation and TCR repertoire. This simple and rapid method of stimulating TIL cells during culture is utilized for both in vitro and in vivo gene transfer protocols.

As an alternate means for stimulating TIL in culture, tumor associated antigenic peptides may be added directly to the TIL culture.

i. Stimulation of TIL with Transfected Neoplastic Cells To culture TIL with transfected neoplastic cells, neoplastic cells were transfected, for example, with pMP6-IL2, and irradiated. Twenty-four hours after irradiation, the transfected cells were washed, harvested by trypsinization, pelleted by centrifugation, and resuspended in culture media. The transfected and irradiated neoplastic cells were then cultured with TIL.

Tumor specificity was retained by the TIL during culture and expansion.

Accordingly, tumor cells (both autologous and HLA matched allogeneic) were used to re-stimulate selected TIL during the expansion phase. This is of significant value because the specificity of T cells for their target is sometimes known to diminish during the course of expansion.

Thus, tumor cells themselves were genetically modified, for example with a composition comprising liposome and pMP6-IL2, to further increase their antigenicity.

Long term culture of TIL often induced polyclonal expansion, with a diminution of tumor specificity by the expanded cells. As shown in FIG. 13, when expanded TIL were stimulated with autologous tumor, the specificity was enhanced. The specificity of TIL stimulated with IL-2 transduced tumor was greater than with unmodified tumor as assessed by TCR repertoires. The enhanced specificity of TIL cultured/stimulated with transfected tumor was particularly notable for data obtained past 30 days of culture.

The data demonstrated that cationic liposomes complexed to an AAV plasmid efficiently transfected primary tumor cells as well as cultured tumor cell lines. Up to 50% of the transfected cells expressed IL-2 as assessed by intracellular IL-2 levels, and the duration of expression was up to 30 days. Irradiation of tumor cells after transfection did not alter transgene expression levels.

TCR analysis demonstrated expansion of tumor-specific T cells; these tumor-specific T cells having been affected by culture of bulk expanded TIL with gene modified autologous tumor.

b. Proliferation of TIL Following Transfection with the IL2 Gene

For the data depicted in FIG. 14, breast TIL were isolated from pleural effusion with subject CD8 devices, and cultured for three weeks in media containing 600 IU/ml IL-2. Analogous experiments were performed with TIL from ovarian tumor; the results were consistent with the results obtained with breast tumor TIL.

Approximately $10\times10^6$ TIL cells were transfected with various compositions comprising pMP6-IL2 DNA:liposome complexes. Two compositions of liposomes, "RPR DDAB" (Nattermann Phospholipid GmBH, Cologne, Germany) and "1100–28" (Applied Immune Sciences, Inc., Santa Clara, Calif.) were tested. The RPR DDAB liposomes had a DDAB:DOPE ratio of 1:1; the 1100–28 liposomes had a DDAB:DOPE ratio of 1:0.6. The transfected TIL cells were then cultured without any exogenous IL2; positive controls were cultured in the presence of 600 IU/ml IL-2.

Five days post-transfection, transfected and untransfected groups were labelled with $^3$H thymidine and assessed for incorporation. The counts from the positive controls were established as 100 percent. Percent growth ranged from 40–80% for the RPR DDAB liposome-transfected groups, and from 40–60% for the 1100–28 liposome group.

The data represented in FIG. 14 demonstrates that breast cancer TIL, when transfected with the IL-2 gene, did not require exogenous IL-2 to maintain proliferation in vitro.

c. Thy 1.2 Gene Expression in TIL

For the data illustrated in FIG. 15, breast cancer TIL were transfected with pMP6 plasmid containing the neomycin resistance gene and the murine Thy 1.2 gene (pMP6/neo/Thy1.2), as an alternate embodiment of the pMP6 plasmid which contained the IL-2 gene. The pMP6/neo/Thy1.2 plasmid was complexed to DDAB:DOPE liposomes. The liposome compositions were the same compositions as those described for the data depicted in FIG. 14. On day 2, the transfected cells were stained with anti-Thy1.2 PE antibodies (Pharmingen, San Diego, Calif.) and analyzed by flow cytometry. As depicted in FIG. 15, the mouse T cell surface marker Thy1.2 was expressed efficiently in transfected human CD8$^+$ TIL.

d. Transgene Expression in Irradiated Human Melanoma Tumor Cells Following Transfection The following data was obtained by transfection of tumor cells with pMP6-IL2. These data demonstrated that tumor cells were successfully gene modified. In addition to DDAB:DOPE, other lipid compositions were also utilized. These various lipid compositions successfully produced lipofection and subsequent cytokine expression.

Melanoma cells were isolated from metastatic foci by following enzymatic digestion methodologies known to those of ordinary skill in the art. Cells were grown in DMEM supplemented with 5–10% fetal calf serum and maintained in culture for a time period of between 5 days to 8 years.

In preparation for lipofection, tumor cells were plated onto 60 mm dishes at a volume of $5\times10^5$ cells/dish. The day following plating, liposomes comprising 10–30 nmol of cationic lipid and 2–10 μg of DNA were admixed and transferred in serum-free media to the adherent monolayers. Cells were incubated for 1–5 hours and FCS was added to the media.

Various liposome preparations were employed successfully, including: DMRIE:DOPE in a 1:1 molar ratio (Vical, San Diego, Calif.); DOSPA:DOPE, 3:1 mass ratio (Gibco, Gaithersberg, Md.) and DDAB:DOPE in a 1:2 molar ratio.

The transfected cells were exposed to lethal levels of x-irradiation (5000 rads) 24 hours following lipofection. Supernatants were collected at 72 hours; thereafter IL-2 levels were measured by ELISA in accordance with information known to those of ordinary skill in the art. The highest level of IL-2 expression obtained with each liposome preparation is listed in Table 5.

Accordingly, high-level expression (>5,000 pg/ml) was detected in nonproliferating viable cells up to 26 days following irradiation.

TABLE 5

| Cell Line | LIPOSOMES | | |
|---|---|---|---|
| | DMRIE:DOPE | DOSPA:DOPE | DDAB:DOPE |
| | IL-2 Levels (picograms/ml) | | |
| DM92 | 33,275 | 12,650 | 1238 |
| DM175 | 24,968 | 5,758 | not tested |
| DM208 | 10,650 | 9,100 | 8,900 |
| DM319 | 26,022 | 35,150 | 31,769 |
| DM336 | 24,967 | not tested | 15,775 |
| DM336 | not tested | 18,730 | 8,713 |
| DM377 | 5,504 | 3,546 | not tested |

These data demonstrate successful transfection of human melanoma cell lines via nonviral, liposome-mediated delivery of plasmid pMP6-IL2. Transfection resulted in significant production of IL-2 following lethal irradiation.

e. Extracellular Assays of Transgene Expression in a Prostate Tumor Cell Line Following Transfection with Various Plasmid Constructs To compare the level and duration of transgene expression following transfections with different plasmid constructs, the prostate tumor cell line, R3327, was transfected with 10 μg standard plasmid (pBC12/CMV-IL2) or 10 μg AAV plasmid (pA CMV-IL2) complexed to 10 nmole DDAB as DDAB:DOPE 1:2 liposomes.

Supernatants were collected at various time points and assayed by ELISA for IL-2 levels. For the data shown in FIG. 10, IL-2 levels were expressed as pg/ml/$10^6$ cells in 24 hrs of culture. Transfection with AAV plasmid produced IL-2 levels significantly higher than with standard plasmid. In addition, transfection with AAV plasmid caused production of IL-2 for at least 30 days, in contrast to only 7 days with standard IL-2 plasmid.

FIG. 17 depicts Southern blot analysis of chromosomal DNA from R3327 cells transfected with an AAV plasmid (pACMV-IL2) or the standard plasmid (pBC12/CMV-IL2). The blot was probed with the 0.685 kb Bam HI/Hind III fragment of the IL-2 gene. In FIG. 17, control (C) is DNA from untransfected cells. The IL-2 insert is shown in the last lane.

f. Intracellular Assays of Transgene Expression in a Prostate Tumor Cell Line Following Transfection with AAV Plasmid Constructs.

The prostate cell line R3327 was transfected with AAV IL-2 plasmid (such as pACMV-IL2) complexed with DDAB:DOPE liposomes; the liposomes in a 1:1 or 1:2 DDAB:DOPE composition ratio. The DNA:liposome ratio was 10 μg DNA:10 nmole DDAB in both groups.

Transfected cells were stained at various time points for intracellular IL-2 protein levels using a modified flow cytometry procedure as described herein; the results are shown in FIG. 18. The data in FIG. 18 are represented as percent positive cells expressing IL-2 protein. Untransfected cells were used as negative controls and the values of controls were subtracted from the values of transfected groups.

g. Transgene Expression in Primary Tumor Cells.

AAV plasmid-liposome complexes were employed to transfect various primary tumor cells. One lung, one ovarian, and two breast tumor samples were isolated from fresh tumor biopsies. Tumor cells were cultured in RPMI-1640 media supplemented with 10% FBS for 2–3 weeks prior to the transfection.

The primary tumor cells were transfected with 10 μg of plasmid (such as pACMV-IL2) complexed to 10 nmoles of DDAB as DDAB:DOPE 1:1. Supernatants were collected on day 2 and 3. IL-2 levels were measured by ELISA; the results are depicted in FIG. 6 where IL-2 levels are expressed as pg/ml/$10^6$ cells in 24 hours of culture.

h. Transgene Expression Following Irradiation of Primary Breast Tumor Cells and Prostate Tumor Cell Line Cells.

To determine the effect of irradiation on gene expression, primary breast tumor cells and cells of a prostate cell line (R3327) were transfected with a composition comprising pACMV-IL2 and DDAB:DOPE liposome complexes, and assessed for gene expression post lethal irradiation. The data for the tumor cell line is shown in FIG. 19A, and the data for the primary tumor cells is in FIG. 19B. In these studies, the transgene was for IL-2. On day 2, an aliquot of the cells was subjected to 6000 r using a $^{60}$Co irradiator and then returned to culture. Supernatants were collected 24, 48, 72 and 96 hrs after irradiation and tested for IL-2 levels. As shown in FIG. 19, lethal irradiation following transfection did not inhibit transgene expression. In FIG. 19, IL-2 levels are expressed as pg/ml/$10^6$ cells in 24 hr culture.

IV. Discussion

In the present studies, the AAV plasmid which contained transgene and AAV terminal repeats was used as a DNA vector, and cationic liposomes were used as carrier molecules. It was demonstrated that the AAV plasmid DNA:liposome complexes efficiently transfected primary tumor cells, cultured cell lines, primary lymphoid cells, and CD34$^+$ stem cells. It was also demonstrated that, in the absence of any recombinant virus (producible from rep and cap capsid particles in adenoviral infected cells), integration with high level and sustained expression of transgene was achieved by the elegant transfection process.

In addition to high levels of expression, the combination of AAV plasmid:liposomes disclosed herein induced long-term (up to 30 days) expression of genes (FIGS. 5a–b), in contrast to the transient expression demonstrated by typical liposome-mediated transfection. Notably, sustained expression was demonstrated in the AAV plasmid lipofected group, as well as in the recombinant AAV transduced group (FIGS. 5a–b). Moreover, ten-fold higher levels of expression were observed with AAV plasmid as compared to standard plasmid transfection, as shown in FIGS. 4a–b.

Under the test conditions disclosed herein, there was no difference in efficiency between optimal AAV transduction and maximal AAV plasmid:liposome transfection. Concerning the time-course of expression, cationic liposomes had previously been shown to mediate only transient expression of standard plasmid DNA in mammalian cell types (Felgner, P. L., et al., "A highly efficient, lipid-mediated DNA transfection procedure," *Proc. Natl. Acad. Sci. USA* (1987) 84:7413–7417; Rose, J. K., et al., "A new cationic liposome reagent mediating nearly quantitative transfection of animal cells," *Biotechniques* (1991) 10:520–525). Moreover, concerning the efficiency of integration, much lower efficiency of integration into the host genome was observed in former liposome-mediated transfection as compared to the results disclosed herein (Shaefer-Ridder, M., et al., "Liposomes as gene carriers: Efficient transfection of mouse L cells by thymidine kinase gene," *Science* (1982) 215:166–168). As shown herein, however, cationic liposomes complexed with AAV plasmid DNA carrying the AAV terminal repeats increased the genomic DNA integration, relative to the standard plasmid that lacked only the AAV terminal repeats (ITRs). Liposomes comprising AAV plasmid material delivered the plasmid DNA in the absence of any specific cell surface receptors, and replaced the function of virus in gene delivery.

In the present studies, it was demonstrated that virus vectors can be altogether replaced by liposomes, and efficient expression and integration was attained by utilizing the construct, including the viral elements responsible for both the efficiency and integration. In this manner, production of virus for infection is avoided, thus virtually eliminating the possibility of an adverse recombinant event. The end results were accomplished by use of an elegant transfection process combining AAV plasmid and cationic liposomes.

In a preferred embodiment, the combination of AAV plasmid and cationic liposomes not only transfected the cultured cell lines efficiently, but also transfected primary tumor cells and peripheral blood cells such as T cells and stem cells. These data are noteworthy since most gene therapy strategies involve gene delivery to primary T lymphocytes or tumor cells. Previously, these strategies have primarily relied upon transgene insertion into retroviral or DNA virus vectors. A fundamental disadvantage of the retroviral system is understood to be the inability to transfect non-dividing primary cells. The present studies have shown that cationic liposomes comprising AAV material mediated transfection of both dividing and non-dividing cell types. In accordance with the invention, AAV plasmid:cationic liposomes have provided a highly efficient transfection system that achieved sustained, high-level expression.

Advantageously, plasmid DNA:liposome complexes can be delivered in vivo (such as by intravenous, intraperitoneal and aerosol administration) without any measurable toxicity (Philip, R., et al., "In vivo gene delivery: Efficient transfection of T lymphocytes in adult mice," *J. Biol. Chem.* (1993) 268:16087–16090; Stribling, R., et al., "Aerosol Gene Delivery in vivo," *Proc. Natl. Acad. Sci. USA* (1992) 89:11277–11281; Zhu, N., et al., "Systemic gene expression after intravenous DNA delivery into adult mice," *Science* (1993) 261:209–211; Stewart, M. J., et al., "Gene transfer in vivo with DNA-liposome complexes: Safety and acute toxicity in mice," *Human Gene Therapy* (1992) 3:267–275). In accordance with the invention, DNA concentration can be optimized to obtain maximum expression. Thus, gene transfer by use of liposomes comprising AAV material transferred AAV and transgene material into a wide variety of cell types ex vivo, and is of use in vivo as well. These present results are of immense advantage to any gene therapy protocol.

Moreover, various primary neoplastic cell types, neoplastic cell lines, and several T cell subpopulations were transfected with AAV plasmids using DNA:liposome complexes. As shown herein, cationic liposomes facilitated adeno-associated viral (AAV) plasmid transfections into cells. The transfection of primary tumor cells was very appealing since such cells are generally very difficult to transfect. In addition to high level expression, use of AAV plasmid:liposomes induced long term (>30 days) expression of transgene. Moreover, when activated and naive T cells were transfected with IL-2 plasmids, the plasmid was detected in the cells a minimum of 25 days post-transfection in an unselected condition. These findings are in contrast to the short term expression demonstrated with typical liposome mediated transfection using standard plasmids.

Moreover, TIL transfected with cytokine transgene were found to expand without the need for exogenous cytokine. This result is very advantageous since TIL can be provided to patients without the need to treat with systemic IL-2, overcoming the serious side-effects of systemic IL-2 treatment.

IL-2 gene expression in the transfected T cells altered the effects of exogenous IL-2 withdrawal. Notably, IL-2 transfected T cells produced sufficient endogenous IL-2 to maintain their growth and proliferation and to prevent apoptosis that normally occurs with exogenous IL-2 withdrawal from the effector T cells known in the art. The dependence on exogenous IL-2 was eliminated.

Primary breast, lung and ovarian tumor cells were transfectable using AAV plasmid DNA:liposome complexes. Transfected primary and cultured tumor cells were able to express the transgene product even after lethal irradiation.

Embodiments of the present disclosure include that tumor cells (both autologous and HLA matched allogeneic) can be used to re-stimulate selected TIL during the expansion phase. Transfected neoplastic cells are used in tumor vaccination protocols. Typically the transfected neoplastic cells are provided together with a pharmaceutical excipient, as is known in the art. Transfected neoplastic cells are also used to stimulate corresponding TIL cells during culture. Phenotype, cytotoxicity and T cell receptor analyses demonstrated that although TILs initially showed tumor cell specificity when they were isolated from tumor, long term culture in rIL-2 often induced polyclonal expansion and loss of tumor specificity. By culture of TIL in a milieu comprising neoplastic cells, and most preferably transfected neoplastic cells, tumor specificity of the expanded TIL cells was markedly increased.

As used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 5585 base pairs
        ( B ) TYPE: nucleic acid
        ( C ) STRANDEDNESS: double (D) TOPOLOGY: circular (ii) MOLECULE TYPE: cDNA to mRNA (iii) HYPOTHETICAL: NO (iv) ANTI-SENSE: NO (x) PUBLICATION INFORMATION:
(H) DOCUMENT NUMBER: PCT/US94/09774
(I) FILING DATE: 13-SEP-1994

(xi) SEQUENCE DESCRIPTION: SEQ ID NO:1:

| | | | | | | |
|---|---|---|---|---|---|---|
| CGCGCAATTA | ACCCTCACTA | AAGGGAACAA | AAGCTGGGTA | CGATCTGGGC | CACTCCCTCT | 60 |
| CTGCGCGCTC | GCTCGCTCAC | TGAGGACGGG | CGACCAAAGG | TCGCCCGACG | CCCGGGCTTT | 120 |
| GCCCGGGCGG | CCTCAGTGAG | CGAGCGAGCG | CGCAGAGAGG | GAGTGGCCAA | CTCCATCACT | 180 |
| AGGGGTTCCT | GGAGGGGTGG | AGTCGTGACG | TGAATTACGT | CATAGGGTTA | GGGAGGTCCG | 240 |
| CGCAATTAAC | CCTCACTAAA | GGGAACAAAA | GCTGGGTACC | GGGCCCTTCG | ATTCGCCCGA | 300 |
| CATTGATTAT | TGACTAGTTA | TTAATAGTAA | TCAATTACGG | GGTCATTAGT | TCATAGCCCA | 360 |
| TATATGGAGT | TCCGCGTTAC | ATAACTTACG | GTAAATGGCC | CGCCTGGCTG | ACCGCCCAAC | 420 |
| GACCCCGCC | CATTGACGTC | AATAATGACG | TATGTTCCCA | TAGTAACGCC | AATAGGGACT | 480 |
| TTCCATTGAC | GTCAATGGGT | GGAGTATTTA | CGGTAAACTG | CCCACTTGGC | AGTACATCAA | 540 |
| GTGTATCATA | TGCCAAGTAC | GCCCCCTATT | GACGTCAATG | ACGGTAAATG | GCCCGCCTGG | 600 |
| CATTATGCCC | AGTACATGAC | CTTATGGGAC | TTTCCTACTT | GGCAGTACAT | CTACGTATTA | 660 |
| GTCATCGCTA | TTACCATGGT | GATGCGGTTT | TGGCAGTACA | TCAATGGGCG | TGGATAGCGG | 720 |
| TTTGACTCAC | GGGGATTTCC | AAGTCTCCAC | CCCATTGACG | TCAATGGGAG | TTTGTTTTGG | 780 |
| CACCAAAATC | AACGGGACTT | TCCAAAATGT | CGTAACAACT | CCGCCCATT | GACGCAAATG | 840 |
| GGCGGTAGGC | GTGTACGGTG | GGAGGTCTAT | ATAAGCAGAG | CTCGTTTAGT | GAACCGTCAG | 900 |
| ATCGCCTGGA | GACGCCATCC | ACGCTGTTTT | GACCTCCATA | GAAGACACCG | GACCGATCC | 960 |
| AGCCTCCGCG | GCCGGGAACG | GTGCATTGGA | ACGCGGATTC | CCCGTGCCAA | GAGTGACGTA | 1020 |
| AGTACCGCCT | ATAGAGTCTA | TAGGCCCACC | CCCTTGGCTT | CTTATGCGAC | GGATCAATTC | 1080 |
| GCTGTCTGCG | AGGGCCAGCT | GTTGGGGTGA | GTACTCCCTC | TCAAAAGCGG | GCATGACTTC | 1140 |
| TGCGCTAAGA | TTGTCAGTTT | CCAAAAACGA | GGAGGATTTG | ATATTCACCT | GGCCCGCGGT | 1200 |
| GATGCCTTTG | AGGGTGGCCG | CGTCCATCTG | GTCAGAAAAG | ACAATCTTTT | TGTTGTCAAG | 1260 |
| CTTGAGGTGT | GGCAGGCTTG | AGATCTGGCC | ATACACTTGA | GTGACAATGA | CATCCACTTT | 1320 |
| GCCTTTCTCT | CCACAGGTGT | CCACTCCCAG | GTCCAACGAT | CCACTAGTTC | TAGTACCAGC | 1380 |
| TGCTAGAGCT | TGGTAAGTGA | CCAGCTACAG | TCGGAAACCA | TCAGCAAGCA | GGTATGTACT | 1440 |
| CTCCAGGGTG | GGCCTGGCTT | CCCCAGTCAA | GACTCCAGGG | ATTTGAGGGA | CGCTGTGGGC | 1500 |
| TCTTCTCTTA | CATGTACCTT | TTGCTAGCCT | CAACCCTGAC | TATCTTCCAG | GTCATTGTTC | 1560 |
| CAACATGGCC | CTGTGGATCG | ACAGGATGCA | ACTCCTGTCT | TGCATTGCAC | TAAGTCTTGC | 1620 |
| ACTTGTCACA | AACAGTGCAC | CTACTTCAAG | TTCTACAAAG | AAAACACAGC | TACAACTGGA | 1680 |
| GCATTTACTG | CTGGATTTAC | AGATGATTTT | GAATGGAATT | AATAATTACA | AGAATCCCAA | 1740 |
| ACTCACCAGG | ATGCTCACAT | TTAAGTTTTA | CATGCCCAAG | AAGGCCACAG | AACTGAAACA | 1800 |
| TCTTCAGTGT | CTAGAAGAAG | AACTCAAACC | TCTGGAGGAA | GTGCTAAATT | TAGCTCAAAG | 1860 |
| CAAAAACTTT | CACTTAAGAC | CCAGGGACTT | AATCAGCAAT | ATCAACGTAA | TAGTTCTGGA | 1920 |
| ACTAAAGGGA | TCTGAAACAA | CATTCATGTG | TGAATATGCT | GATGAGACAG | CAACCATTGT | 1980 |

| | | | | | | |
|---|---|---|---|---|---|---|
| AGAATTTCTG | AACAGATGGA | TTACCTTTTG | TCAAAGCATC | ATCTCAACAC | TGACTTGATA | 2040 |
| ATTAAGTGCT | TCCCACTTAA | AACATATCAG | GGATCGATCC | AGACATGATA | AGATACATTG | 2100 |
| ATGAGTTTGG | ACAAACCACA | ACTAGAATGC | AGTGAAAAAA | ATGCTTATT | TGTGAAATTT | 2160 |
| GTGATGCTAT | TGCTTTATTT | GTAACCATTA | TAAGCTGCAA | TAAACAAGTT | AACAACAACA | 2220 |
| ATTGCATTCA | TTTTATGTTT | CAGGTCAGG | GGGAGGTGTG | GGAGGTTTTT | TAAAGCAAGT | 2280 |
| AAAACCTCTA | CAAATGTGGT | ATGGCTGATT | ATGATCCGGC | TGCCTCGCGC | GTTTCGGTGA | 2340 |
| TGACGGTGAA | AACCTCTGAC | ACATGCAGCT | CCCGGAGACG | GTCACAGCTT | GTCTGTAAGC | 2400 |
| GGATGCCGGG | AGCAGACAAG | CCCGTCAGGG | CGCGTCAGCG | GGTGTTGGCG | GGTGTCGGGG | 2460 |
| CGCAGCCATG | AGGTCGACTC | TAGTAGAGCG | GCCGCCACCG | CGGTGGAGCT | CCAATTCGCC | 2520 |
| CTATAGTGAG | TCGTATTACG | CGCGTCGAGT | CTAGAGAGCT | CGGGCCCAAG | CTTGGTACCC | 2580 |
| ATGGCTACGT | AGATAAGTAG | CATGGCGGGT | TAATCATTAA | CTACAAGGAA | CCCCTAGTGA | 2640 |
| TGGAGTTGGC | CACTCCCTCT | CTGCGCGCTC | GCTCGCTCAC | TGAGAGACCG | CGACCAAAGG | 2700 |
| TCGCCCGACG | CCCGGGCTTT | GCCCGGGCGG | CCTCAGTGAG | CGAGCGAGCG | CGCAGAGAGG | 2760 |
| GACAGATCCA | ATTCGCCCTA | TAGTGAGTCG | TATTACGCGC | GCTCACTGGC | CGTCGTTTTA | 2820 |
| CAACGTCGTG | ACTGGGAAAA | CCCTGGCGTT | ACCCAACTTA | ATCGCCTTGC | AGCACATCCC | 2880 |
| CCTTTCGCCA | GCTGGCGTAA | TAGCGAAGAG | GCCCGCACCG | ATCGCCCTTC | CAACAGTTG | 2940 |
| CGCAGCCTGA | ATGGCGAATG | GGACGCGCCC | TGTAGCGGCG | CATTAAGCGC | GGCGGGTGTG | 3000 |
| GTGGTTACGC | GCAGCGTGAC | CGCTACACTT | GCCAGCGCCC | TAGCGCCCGC | TCCTTTCGCT | 3060 |
| TTCTTCCCTT | CCTTTCTCGC | CACGTTCGCC | GGCTTTCCCC | GTCAAGCTCT | AAATCGGGGG | 3120 |
| CTCCCTTTAG | GGTTCCGATT | TAGTGCTTTA | CGGCACCTCG | ACCCCAAAAA | ACTTGATTAG | 3180 |
| GGTGATGGTT | CACGTAGTGG | GCCATCGCCC | TGATAGACGG | TTTTTCGCCC | TTTGACGTTG | 3240 |
| GAGTCCACGT | TCTTTAATAG | TGGACTCTTG | TTCCAAACTG | GAACAACACT | CAACCCTATC | 3300 |
| TCGGTCTATT | CTTTTGATTT | ATAAGGGATT | TTGCCGATTT | CGGCCTATTG | GTTAAAAAAT | 3360 |
| GAGCTGATTT | AACAAAAATT | TAACGCGAAT | TTTAACAAAA | TATTAACGCT | TACAATTTAG | 3420 |
| GTGGCACTTT | TCGGGGAAAT | GTGCGCGGAA | CCCCTATTTG | TTTATTTTTC | TAAATACATT | 3480 |
| CAAATATGTA | TCCGCTCATG | AGACAATAAC | CCTGATAAAT | GCTTCAATAA | TATTGAAAAA | 3540 |
| GGAAGAGTAT | GAGTATTCAA | CATTTCCGTG | TCGCCCTTAT | TCCCTTTTTT | GCGGCATTTT | 3600 |
| GCCTTCCTGT | TTTTGCTCAC | CCAGAAACGC | TGGTGAAAGT | AAAAGATGCT | GAAGATCAGT | 3660 |
| TGGGTGCACG | AGTGGGTTAC | ATCGAACTGG | ATCTCAACAG | CGGTAAGATC | CTTGAGAGTT | 3720 |
| TTCGCCCCGA | AGAACGTTTT | CCAATGATGA | GCACTTTTAA | AGTTCTGCTA | TGTGGCGCGG | 3780 |
| TATTATCCCG | TATTGACGCC | GGGCAAGAGC | AACTCGGTCG | CCGCATACAC | TATTCTCAGA | 3840 |
| ATGACTTGGT | TGAGTACTCA | CCAGTCACAG | AAAAGCATCT | TACGGATGGC | ATGACAGTAA | 3900 |
| GAGAATTATG | CAGTGCTGCC | ATAACCATGA | GTGATAACAC | TGCGGCCAAC | TTACTTCTGA | 3960 |
| CAACGATCGG | AGGACCGAAG | GAGCTAACCG | CTTTTTTGCA | CAACATGGGG | GATCATGTAA | 4020 |
| CTCGCCTTGA | TCGTTGGGAA | CCGGAGCTGA | ATGAAGCCAT | ACCAAACGAC | GAGCGTGACA | 4080 |
| CCACGATGCC | TGTAGCAATG | GCAACAACGT | TGCGCAAACT | ATTAACTGGC | GAACTACTTA | 4140 |
| CTCTAGCTTC | CCGGCAACAA | TTAATAGACT | GGATGGAGGC | GGATAAAGTT | GCAGGACCAC | 4200 |
| TTCTGCGCTC | GGCCCTTCCG | GCTGGCTGGT | TTATTGCTGA | TAAATCTGGA | GCCGGTGAGC | 4260 |
| GTGGGTCTCG | CGGTATCATT | GCAGCACTGG | GGCCAGATGG | TAAGCCCTCC | CGTATCGTAG | 4320 |
| TTATCTACAC | GACGGGGAGT | CAGGCAACTA | TGGATGAACG | AAATAGACAG | ATCGCTGAGA | 4380 |

-continued

| | | | | | | |
|---|---|---|---|---|---|---|
| TAGGTGCCTC | ACTGATTAAG | CATTGGTAAC | TGTCAGACCA | AGTTTACTCA | TATATACTTT | 4440 |
| AGATTGATTT | AAAACTTCAT | TTTTAATTTA | AAAGGATCTA | GGTGAAGATC | CTTTTTGATA | 4500 |
| ATCTCATGAC | CAAAATCCCT | TAACGTGAGT | TTTCGTTCCA | CTGAGCGTCA | GACCCCGTAG | 4560 |
| AAAAGATCAA | AGGATCTTCT | TGAGATCCTT | TTTTTCTGCG | CGTAATCTGC | TGCTTGCAAA | 4620 |
| CAAAAAAACC | ACCGCTACCA | GCGGTGGTTT | GTTGCCGGA | TCAAGAGCTA | CCAACTCTTT | 4680 |
| TTCCGAAGGT | AACTGGCTTC | AGCAGAGCGC | AGATACCAAA | TACTGTCCTT | CTAGTGTAGC | 4740 |
| CGTAGTTAGG | CCACCACTTC | AAGAACTCTG | TAGCACCGCC | TACATACCTC | GCTCTGCTAA | 4800 |
| TCCTGTTACC | AGTGGCTGCT | GCCAGTGGCG | ATAAGTCGTG | TCTTACCGGG | TTGGACTCAA | 4860 |
| GACGATAGTT | ACCGGATAAG | GCGCAGCGGT | CGGGCTGAAC | GGGGGGTTCG | TGCACACAGC | 4920 |
| CCAGCTTGGA | GCGAACGACC | TACACCGAAC | TGAGATACCT | ACAGCGTGAG | CTATGAGAAA | 4980 |
| GCGCCACGCT | TCCCGAAGGG | AGAAAGGCGG | ACAGGTATCC | GGTAAGCGGC | AGGGTCGGAA | 5040 |
| CAGGAGAGCG | CACGAGGGAG | CTTCCAGGGG | GAAACGCCTG | GTATCTTTAT | AGTCCTGTCG | 5100 |
| GGTTTCGCCA | CCTCTGACTT | GAGCGTCGAT | TTTTGTGATG | CTCGTCAGGG | GGGCGGAGCC | 5160 |
| TATGGAAAAA | CGCCAGCAAC | GCGGCCTTTT | TACGGTTCCT | GGCCTTTTGC | TGGCCTTTTG | 5220 |
| CTCACATGTT | CTTTCCTGCG | TTATCCCCTG | ATTCTGTGGA | TAACCGTATT | ACCGCCTTTG | 5280 |
| AGTGAGCTGA | TACCGCTCGC | CGCAGCCGAA | CGACCGAGCG | CAGCGAGTCA | GTGAGCGAGG | 5340 |
| AAGCGGAAGA | GCGCCCAATA | CGCAAACCGC | CTCTCCCCGC | GCGTTGGCCG | ATTCATTAAT | 5400 |
| GCAGCTGGCA | CGACAGGTTT | CCCGACTGGA | AAGCGGGCAG | TGAGCGCAAC | GCAATTAATG | 5460 |
| TGAGTTAGCT | CACTCATTAG | GCACCCCAGG | CTTTACACTT | TATGCTTCCG | GCTCGTATGT | 5520 |
| TGTGTGGAAT | TGTGAGCGGA | TAACAATTTC | ACACAGGAAA | CAGCTATGAC | CATGATTACG | 5580 |
| CCAAG | | | | | | 5585 |

What is claimed is:

1. A method for introducing a genetic sequence of interest into a host cell, said method comprising steps of:
   providing a composition comprising a cationic liposome; and
   a plasmid including at least one inverted terminal repeat from adeno-associated virus and a promoter other than an adeno-associated virus promoter, and a genetic sequence of interest; and
   contacting the composition with a host cell which comprises genetic material, whereby the genetic sequence of interest is introduced into the host cell.

2. The method of claim 1 wherein the host cell is selected from the group consisting of a CD34$^+$ stem cell, a T cell, a cell of a tumor cell line, and a primary tumor cell.

3. The method of claim 2 wherein the host cell is selected from the group consisting of a tumor infiltrating lymphocyte, CD3$^+$ cell, CD4$^+$ cell, and CD8$^+$ cell.

4. The method of claim 2 wherein the cell is from a tumor cell line which is selected from the group consisting of a bladder tumor cell line, a prostate tumor cell line, a B lymphoma cell line, and an embryonic kidney tumor cell line.

5. The method of claim 1 wherein the plasmid is pMP6-IL2.

6. The method of claim 1 further comprising a step of integrating the genetic material of interest into the genetic material of the host cell.

7. A method for treating a human patient to relieve or eliminate a medical condition, said method comprising steps of:
   providing a patient with a condition;
   providing a composition comprising a cationic liposome; and
   a plasmid including at least one inverted terminal repeat from adeno-associated virus and a promoter other than an adeno-associated virus promoter, and a genetic sequence of interest; and,
   contacting the composition with a host cell, whereby the genetic sequence of interest is introduced into the host cell: where the contacting is in vivo and the host cell is a cell of the patient; or where the contacting is ex vivo, and the host cell is autologous or allogeneic, and further comprising a step of delivering the host cell comprising the introduced genetic sequence of interest to the patient,
   wherein the genetic sequence of interest is expressed resulting in treatment of the patient's condition by relieving or eliminating the condition.

8. The method of claim 7 wherein the step of providing a patient provides a patient with a condition selected from the group consisting of a neoplasm, an infection, an autoimmune condition, and a genetic abnormality.

9. The method of claim 8 wherein the step of providing a patient provides a patient with a genetic abnormality which comprises a missing or defective gene.

10. The method of claim 7 wherein the step of providing a composition comprising a cationic liposome; and
    a plasmid including at least one inverted terminal repeat from adeno-associated virus and a promoter other than an adeno-associated virus promoter, and a genetic sequence of interest, provides a genetic sequence of interest encoding a product selected from the group consisting of a peptide, an anti-sense oligonucleotide, and RNA.

11. The method of claim 7 wherein the plasmid is pMP6-IL2.

12. The method of claim 7 wherein the genetic sequence of interest is selected from the group consisting of genetic sequences encoding a product selected from the group consisting of a cytokine, a costimulatory factor, a MHC class I molecule, a tumor-specific antigen, and a tumor-associated antigen.

13. The method of claim 7 wherein the step of providing a patient provides a patient with a malignant neoplastic condition; and wherein the genetic sequence of interest comprises the MDR I gene.

14. The method of claim 7 wherein the step of contacting the composition with a host cell comprises contacting with a host cell that is selected from the group consisting of a neoplastic cell, a bone marrow hematopoietic cell, and a peripheral blood cell.

15. The method of claim 14 wherein the step of contacting the composition with a host cell comprises contacting with a host cell that is selected from the group consisting of a tumor infiltrating lymphocyte, a cell of a tumor cell line, and a primary tumor cell.

16. An expression vector comprising the genetic sequence of plasmid pMP6.

17. The expression vector of claim 16 which further comprises a genetic sequence of interest.

18. A cultured cell that is transfected with the expression vector of claim 17.

19. The cell of claim 18 which is selected from the group consisting of a peripheral blood cell, a bone marrow cell, a tumor infiltrating lymphocyte, a tumor cell line cell, and a primary tumor cell.

20. An expression vector comprising SEQ ID No: 1.

21. A cultured cell that is transfected with the expression vector of claim 20.

22. The cell of claim 21 which is selected from the group consisting of a peripheral blood cell, a bone marrow cell, a tumor infiltrating lymphocyte, a tumor cell line cell, and a primary tumor cell.

23. A method for producing a protein, said method comprising steps of:

providing a composition comprising a cationic liposome; and a plasmid including at least one inverted terminal repeat from adeno-associated virus and a promoter other than an adeno-associated virus promoter, and a genetic sequence of interest;

contacting the composition with a host cell which comprises genetic material, whereby the genetic sequence of interest is introduced into the host cell; and, expressing a protein encoded by the genetic sequence of interest.

24. The method of claim 23 wherein the host cell is a CD34$^+$ stem cell, a T cell, a cell of a tumor cell line, or a primary tumor cell.

25. The method of claim 24 wherein the host cell is: a tumor infiltrating lymphocyte, CD3$^+$, CD4$^+$, or CD8$^+$.

26. The method of claim 24 wherein the cell is from a tumor cell line which is: a bladder, a prostate, a B lymphoma, or an embryonic kidney tumor cell line.

27. The method of claim 23 wherein the providing step provides a composition that comprises cationic lipid.

28. The method of claim 23 wherein the plasmid is-pMP6-IL2.

29. The method of claim 23 further comprising a step of integrating the genetic material of interest into the genetic material of the host cell.

30. The method of claim 23 wherein the step of expressing a protein expresses a lymphokine analogue.

31. The method of claim 23 wherein the step of expressing a protein expresses IL-2.

32. The method of claim 29 wherein the step of expressing a protein expresses a protein selected from the group consisting of β-galactosidase, chloramphenicol-acetyl-transferase, and MDR I.

33. A method for introducing a genetic sequence of interest into a host cell, said method comprising the steps of:

providing a composition comprising a cationic liposome; and a plasmid including at least one inverted terminal repeat from adeno-associated virus and a promoter other than an adeno-associated virus promoter, and a genetic sequence of interest; and, contacting the composition with a host cell which comprises genetic material and which is selected from the group consisting of a CD34$^+$ stem cell, a T cell, a cell of a tumor cell line, and a primary tumor cell, whereby the genetic sequence of interest is introduced into the host cell.

34. A method for introducing a genetic sequence into a host cell comprising the steps of:

providing a composition comprising a cationic liposome and an adeno-associated virus expression vector having: (A) at least one inverted terminal repeat sequence from adeno-associated virus; (B) said genetic sequence; and (C) a promoter for expression of said genetic sequence; and contacting said composition with a host cell selected from the group consisting of unmodified stem cells, unmodified T cells, tumor cell line cells and primary tumor cells to introduce said composition into said host cell;

said expression vector being maintained extra-chromosomally in said host cells for at least about 25 days following said contacting in the absence of selection for host cells containing said expression vector.

35. A method for producing interleukin-2 comprising the steps of:

providing a composition comprising liposome and an adeno-associated virus expression vector having: (A) at least one inverted terminal repeat sequence from adeno-associated virus; (B) a genetic sequence which encodes interleukin-2; and (C) a promoter other than an adeno-associated virus promoter for expression of said genetic sequence;

contacting said composition with a T cell to produce interleukin-2 by expression of said genetic sequence encoding interleukin-2.

36. The method of claim 35 wherein said T cell is a tumor-infiltrating lymphocyte.

37. A method for providing activated tumor-infiltrating lymphocytes to a patient comprising administering to said patient a tumor-infiltrating lymphocyte which expresses interleukin-2 and which is prepared by contacting a composition comprising a tumor-infiltrating lymphocyte with a cationic liposome and an adeno-associated virus expression vector which encodes the genetic sequence for interleukin-2, said expression vector being maintained extrachromasomally in said tumor-infiltrating lymphocyte for at least about 25 days following said contacting in the absence of selection for tumor infiltrating lymphocytes containing said expression vector.

38. A method according to claim 37 wherein said administration is conducted in the absence of systemic administration to the patient of interleukin-2.

39. A composition for genetic manipulation comprising:
a cationic liposome; and
a plasmid including at least one inverted terminal repeat from adeno-associated virus and a promoter other than an adeno-associated virus promoter.

40. The composition of claim 39 wherein the plasmid is pMP6-IL2.

41. The composition of claim 39 wherein the promoter is selected from the group consisting of a CMV immediate-early promoter, a CMV immediate-late promoter, a CMV early promoter, an ADA promoter, and a TK promoter.

42. The composition of claim 39 further comprising a genetic sequence of interest.

43. The composition of claim 42, wherein the genetic sequence of interest comprises a genetic sequence selected from the group consisting of an IL-2 gene and a β-gal gene.

44. Cultured mammalian host cells transfected by the composition of claim 39.

45. The method of claim 1 wherein said promoter other than an adeno-associated virus promoter is a non-parvovirus promoter.

46. In a method for treating an HIV infection in a patient by administering to the patient a composition comprising a plasmid encoding a protein which provides a therapeutic effect and a promoter, the improvement comprising:

(A) said composition comprising: (1) a cationic liposome; and (2) a plasmid including: (a) at least one inverted terminal repeat from adeno-associated virus; (b) a promoter other than an adeno-associated virus promoter; and (c) said protein; to thereby introduce into a host cell within the patient said protein; or (B) said composition comprising an autologous or allogenic host cell into which said composition of (A) has been introduced ex vivo to thereby introduce said protein into the patient wherein said protein provides a therapeutic effect by relieving or eliminating the condition.

47. The method of claim 46 wherein said protein comprises IL-2.

48. The method of claim 46 wherein said host cell is an autologous host cell.

49. The method of claim 46 wherein said host cell is an allogenic host cell.

* * * * *